United States Patent
Miyazaki et al.

(10) Patent No.: US 6,826,251 B1
(45) Date of Patent: Nov. 30, 2004

(54) MULTISLICE X-RAY CT APPARATUS

(75) Inventors: Osamu Miyazaki, Ibararki (JP); Taiga Goto, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 106 days.

(21) Appl. No.: 10/111,170

(22) PCT Filed: Oct. 19, 2000

(86) PCT No.: PCT/JP00/07271

§ 371 (c)(1),
(2), (4) Date: Apr. 22, 2002

(87) PCT Pub. No.: WO01/28425

PCT Pub. Date: Apr. 26, 2001

(30) Foreign Application Priority Data

Oct. 20, 1999 (JP) .......................................... 11-298351
Apr. 4, 2000 (JP) ....................................... 2000-102504
Sep. 29, 2000 (JP) ....................................... 2000-298888

(51) Int. Cl.[7] ............................................. A61B 6/03
(52) U.S. Cl. ........................................... 378/15; 378/4
(58) Field of Search ................................. 378/4, 15, 19, 378/901

(56) References Cited

U.S. PATENT DOCUMENTS

| 5,825,842 | A | * | 10/1998 | Taguchi | .................. | 378/15 |
| 5,974,108 | A | * | 10/1999 | Taguchi et al. | ............... | 378/4 |
| 6,028,908 | A | * | 2/2000 | Taguchi | .................. | 378/15 |
| 6,584,166 | B2 | * | 6/2003 | Taguchi | .................. | 378/19 |

* cited by examiner

*Primary Examiner*—Edward J. Glick
*Assistant Examiner*—Hoon Song
(74) *Attorney, Agent, or Firm*—Antonelli, Terry, Stout & Kraus, LLP

(57) ABSTRACT

A multi-slice x-ray CT apparatus has detectors arranged in rows, and projection data on a cross section of an object can be simultaneously measured, wherein the spiral pitch can be arbitrarily determined. A virtual detector row is virtually defined to compensate for lack of lines if the spiral pitch is larger than the number of pitches, so as to always create a high-quality image even if the relationship between the number of rows of detectors and the spiral pitches changes. The weight determined for the virtual detector row is distributed to the weights of projection data on the actual detectors used when the projection data on the virtual detector row is determined.

24 Claims, 19 Drawing Sheets

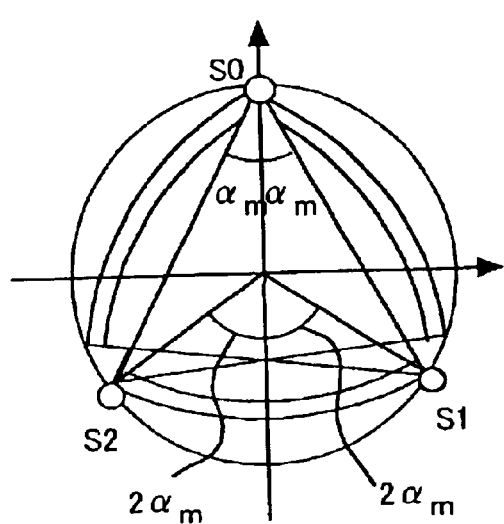
FIG. 7a
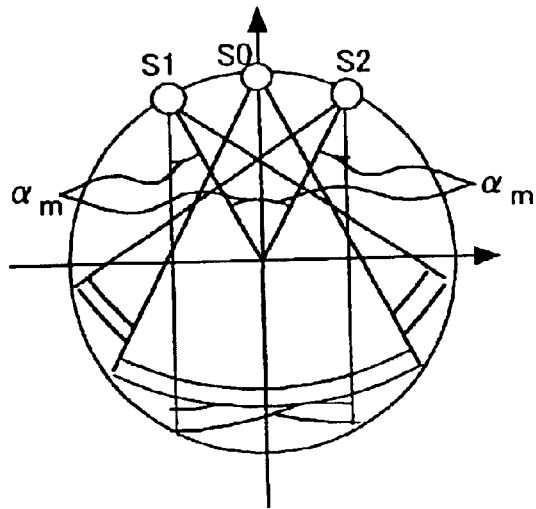
FIG. 7b
FIG. 8
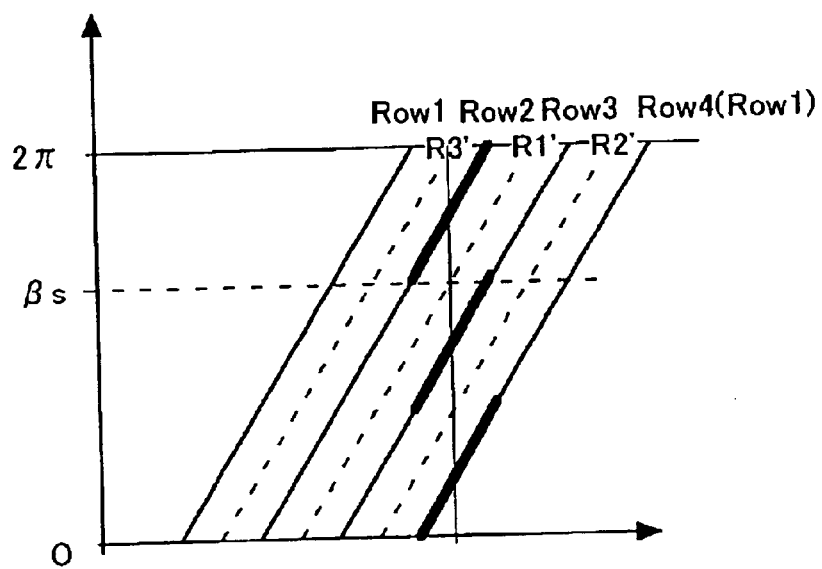

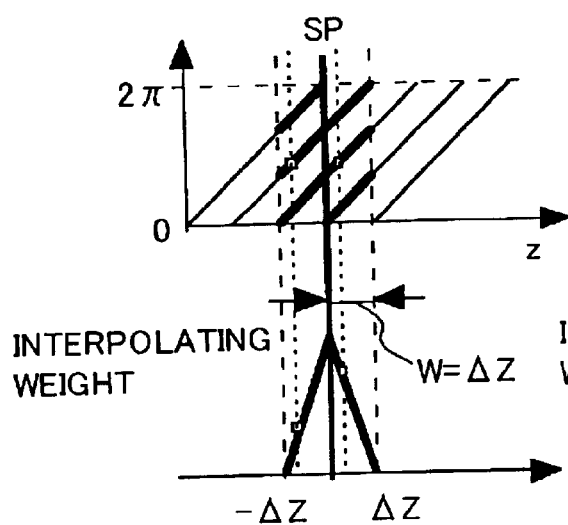
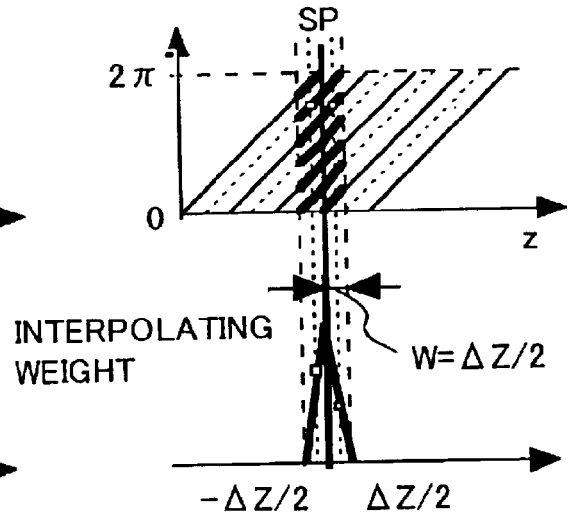
FIG. 9a　　　　　　　　FIG. 9b
FIG. 10
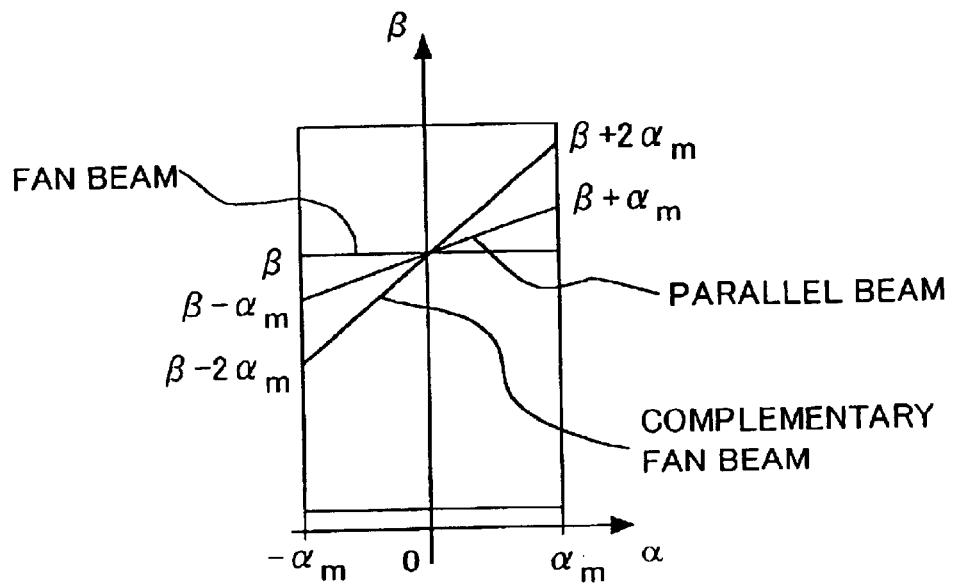

COMPLEMENTARY REGION FOR COMPENSATING WITH VIRTUAL DETECTOR ROWS

COMPLEMENTARY DATA

COMPLEMENTARY DATA

MULTISLICE X-RAY CT APPARATUS

FIELD OF THE INVENTION

The present invention relates to a multi-slice X-ray CT apparatus that is capable of scanning helically (hereinafter referred to as a multi-slice CT); and, more particularly, the invention relates to a multi-slice CT having a correction processing function for performing correction processing of measured spiral projection data.

BACKGROUND OF THE INVENTION

Nowadays, a R/R type (the third generation) CT system is mainly being used. In such a system, an X-ray source and detectors, which are arrayed in a circle so as to point to a focal spot of said x-ray source, are positioned so as to face a space into which the object to be examined is inserted. The x-rays from the x-ray source are collimated to form fan-shaped x-ray beam, and they are irradiated to the imaging plane of the object to be examined. Data acquisition is performed by measuring the attenuated x-rays transmitted through the object to be examined. The procedure for acquisition of data is performed at intervals 0.1~0.5 degree. For example 600~1200 items of projection data are acquired during one revolution.

A detector is comprised of many detector elements, and the output of each detector element is corrected as a digital data value using measurement circuits to compose data (view) of a number of elements at each angle. This view data is successively transferred from a rotation system to a stationary system with respect to the transmitting path. After pre-processing, such as characteristic correction of detector elements, and log conversion of the transferred data to an image processing device in a stationary system, a slice image is reconstructed with a known algorithm, such as a filtered back projection method.

As an one applied example of such an X-ray CT system, a spiral CT (helical CT) apparatus is known which makes it possible to achieve a faster examination when measuring with a rotating x-ray source and detector, together with a moving table for supporting the object to be examined. In such a spiral CT apparatus for scanning spirally around the object to be examined, it is necessary to acquire the projection data at a slice position using interpolation from data acquired spirally for acquiring a specified slice image. Such an interpolation method is disclosed for example in U.S. Pat. No. 4,789,929. By performing such interpolation processing, the presence of a motion artifact can be reduced.

Furthermore, there is a multi-slice CT apparatus that makes it possible to measure a plural number of projection data simultaneously by dividing detectors into a plural number of rows. In such a multi-slice CT, the view is simultaneously corrected for the number of rows. Thus, in case of conventional stationary table scanning, a plural number of slices can be simultaneously imaged. When spiral scanning is performed in such a multi-slice CT, it is necessary to reconstruct the data by performing interpolation processes the same as a single slice, or weighting corresponding to it. U.S. Pat. No. 5,541970 discloses a method which achieves helical correction by composing a weighting coefficient to interpolate with the nearest complementary beam. In addition in Japanese Patent Laid-Open No. 9-285460, a method to increase the continuity by use of a smoothing weighting coefficient in a Z axis direction is proposed. However in such traditional multi-slice CT spiral scanning, it is impossible to cope with the changing of the relationship between the row number of the detectors and the helical pitch, and there is no expansibility, such as increasing the order of interpolation.

Thus, an object of the present invention is to provide a multi-slice CT apparatus that makes it possible to obtain a high quality slice image and that is capable of coping with the changing of the spiral pitch when spiral scanning is performed in a multi-slice CT operation.

Another object of the present invention is to provide a multi-slice CT apparatus with which it is possible to reduce the x-ray dose applied to a patient during a multi-slice CT operation.

SUMMARY OF THE INVENTION

To achieve the above-mentioned objects, a multi-slice CT apparatus according to the present invention has multi-element detectors arranged in a plural number of row in the axial direction, and a moving patient table for supporting the object to be examined for movement in the axial direction. In the apparatus, x-rays transmitted through the object to be examined by a rotating x-ray source are detected by said detectors, and a plural number of spiral projection data are acquired. The apparatus further has correction processing means for performing correction processing of measured spiral projection data, and image reconstruction means for acquiring a slice image reconstructed with corrected projection data.

The correction processing means generates a plural number of different multi-slice spiral weighting to cope with the spiral pitch amount of table movement during one rotation relative to a row interval of said detectors. One of said plural number of multi-slice spiral weighting is selected in accordance with the spiral pitch during measuring to apply spiral projection data for each row, and spiral projection data at each row is combined after weighting is applied.

One embodiment of a multi-slice CT system according to the present invention involves correction processing means which operates to change the weighting region of spiral projection data of a processing target in accordance with the spiral pitch during measurement. Thus, data in the neighborhood of a measuring position can be used as a data for interpolation, and a high quality image can be obtained.

Another embodiment of a multi-slice CT system according to the present invention involves correction processing means which operates to generate a multi-slice spiral weighting coefficient applied to spiral projection data at each row and to combine spiral projection data at each row after said weighting is applied. Such means for generating said multi-slice spiral weighting coefficient sets a virtual detector that is at a different position from the actual detector, and sets multi-slice spiral weighing about all rows of projection data comprising said actual detector and virtual detector.

A virtual detector can be set to make all row number comprising said actual detector and virtual detector be P, when the actual detector row number N is smaller than the spiral pitch P(P>N), and a virtual detector can be positioned between actual detector in the neighborhood. Weighting for applying projection data of said virtual detector can be shared with weighting of projection data at the actual detectors in the neighborhood. On the other hand, a virtual detector can be positioned outside of the measuring region in the axial direction of an actual detector row, and complementary data can be used as projection data of said virtual detector, whereby weighting for said complementary data is shared with projection data of the actual detectors in the neighborhood.

By using the concept of a virtual detector, interpolation for using appropriated weighting is made possible so as to produce an image of high quality, even in a case where the spiral pitch is larger than the detector row number. And, when one slice projection data is acquired with interpolation during multi-slice helical scanning, a discontinuity due to changing of a pair of real measured data for interpolating in a slice is canceled so as to produce an image of high quality.

Furthermore, as another embodiment of a multi-slice CT system according to the present invention, the x-ray source comprises means for controlling the rows of said detectors corresponding to the spiral pitch of the table movement per one rotation relative to a detector row interval. The number of rows can be set appropriately in accordance with the spiral pitch, and the x-ray dose applied to a patient can be reduced by controlling if the row number needs a lot.

BRIEF DESCRIPTION OF THE DRAWINGS

FIG. 7(a) is a diagram showing the relationship between a fan beam and a complementary beam, and FIG. 7(b) is a diagram showing the relationship between parallel beams;

FIG. 8 is a diagram showing one example of multi-slice spiral weighting (inverse phase interpolation);

FIGS. 9(a) and 9(b) are diagrams illustrating the concepts involving same phase interpolation and inverse phase interpolation, respectively;

FIG. 10 is a sonogram showing a fan beam, complementary beam, and parallel beam;

BEST MODE OF CARRYING OUT THE INVENTION

Hereinafter, a multi-slice CT apparatus according to the present invention will be described, based on an exemplary embodiment.

<<Apparatus Composition>>

Figure 1:
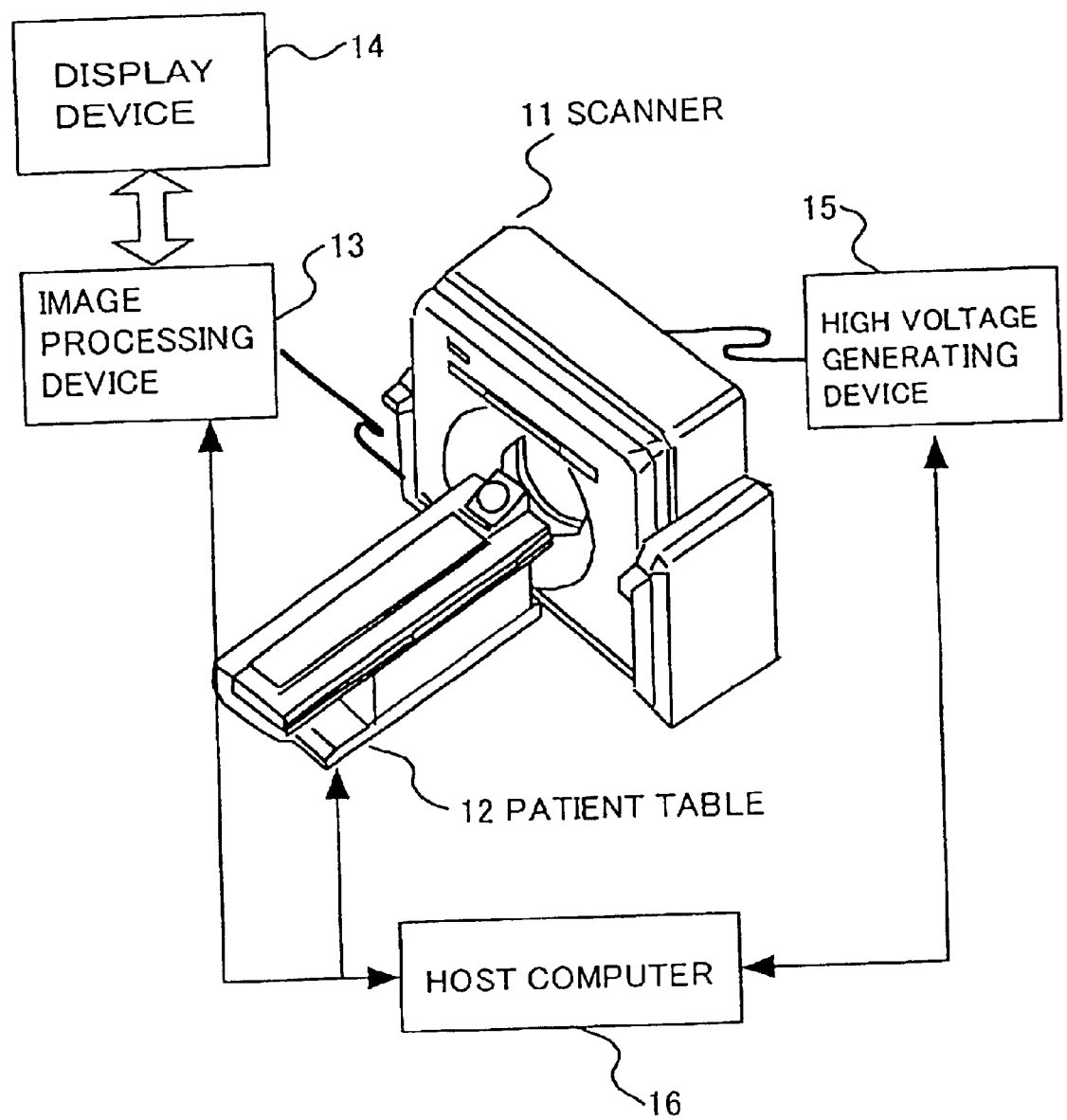
FIG. 1 is a schematic perspective view showing the whole X-ray CT apparatus according to the invention.

FIG. 1 is a diagram showing the basic elements of an x-ray CT apparatus to which the present invention is applied. This X-ray CT apparatus comprises a scanner 11, which has an x-ray generation device(x-ray source), an x-ray detector, measuring circuits and a rotation scanning control system (these elements are not shown in the figure); a patient table 12 for supporting a patient, being the object to be examined, for movement into a measuring space provided in the scanner 11; an image processing device 13 for performing image processing, such as pre processing and reconstruction of data measured in the measuring circuits; a display device 14 for displaying image data to produce a reconstructed image or the like; a high voltage generation device 15 for supplying a high voltage to the x-ray generation device; and a host computer 16 for controlling the entire system.

Figure 2:
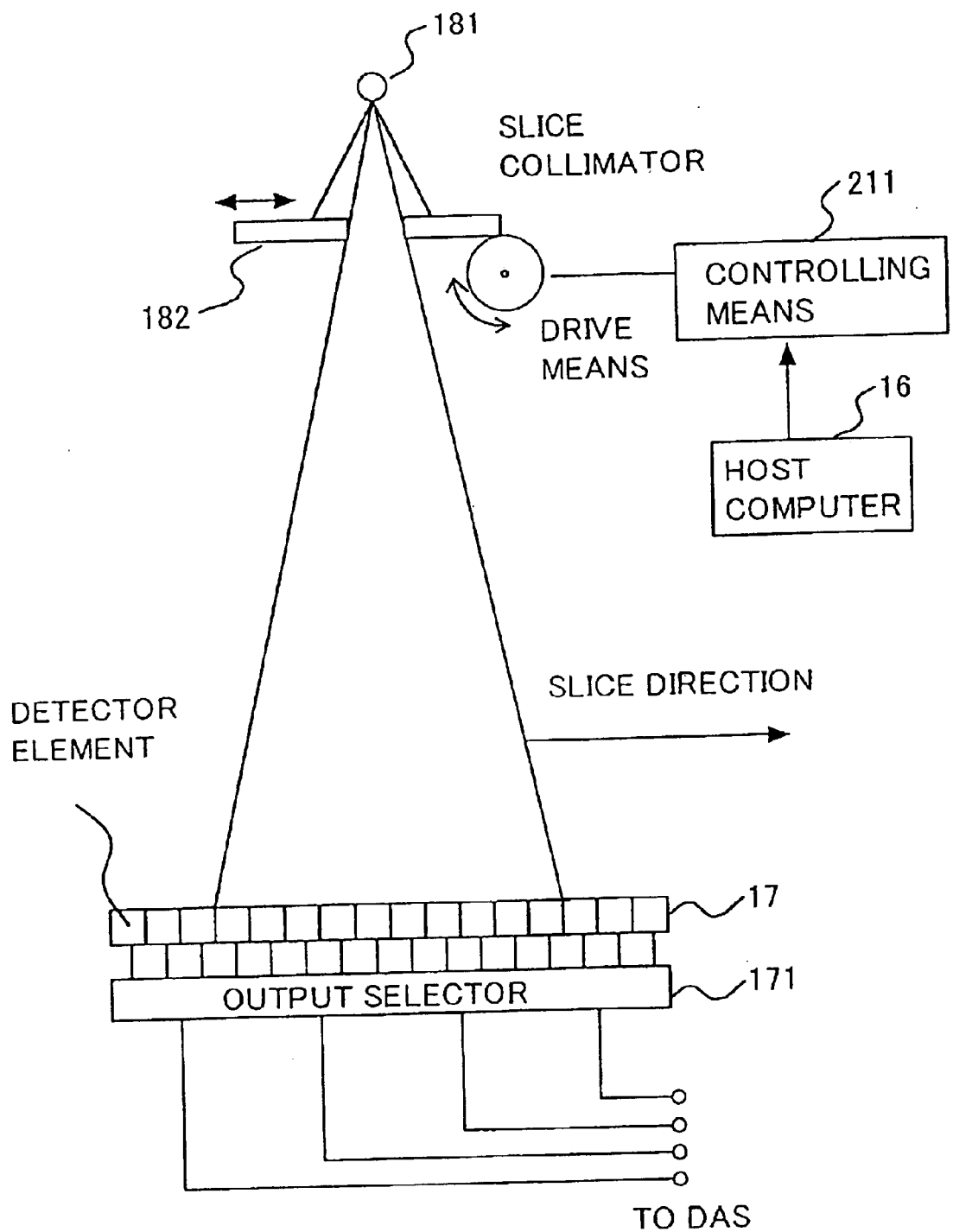
FIG. 2 is a schematic diagram showing one example of a feature of the X-ray CT apparatus of the present invention.

An X-ray detector 17 comprises a detector formed of multi-elements arranged in a plural number of rows in the axial direction (slice direction), as shown in FIG. 2. As shown in the figure, the detector is divided into sixteen rows, and the outputs of the sixteen divided rows are composed to form an arbitrary four output system using output selector 171.

The output of the system is preferably represented by an arbitrary out of 16 rows, and is preferably produced output adding a plural number of rows analogy or digitally. By changing the setting of the four output system, an image of a different slice width characteristic or noise characteristic can be acquired. Hereinafter, the number of selected detector signals is assumed to be four, but the number according to the invention can be larger than four.

The X-ray generation device comprises an x-ray tube 181, a slice collimator 182 for collimating x-rays irradiated from the x-ray tube 181 and for controlling fan beam irradiation to have a predetermined width and a predetermined opening angle. Moreover, the collimator 182 comprises a system for adjusting the width of x-rays in the slice direction. By controlling the width of the fan beam in the slice direction, the number of detector rows can be arbitrarily set. The system for adjusting this width can be controlled using the host computer 16.

The x-ray CT apparatus can move the patient table 12 in the axial direction, measure x-rays transmitted from the object to be examined using the rotating scanner 11(x-ray source and detector), and acquire spiral projection data of a selected detector row number (in this case four system). Acquisition of the helical projection data is known as helical scanning. The helical pitch P is defined as the amount $t(y/\Delta Z)$ of table movement during one rotation relative to the detector row interval $\Delta Z$.

Figure 3:
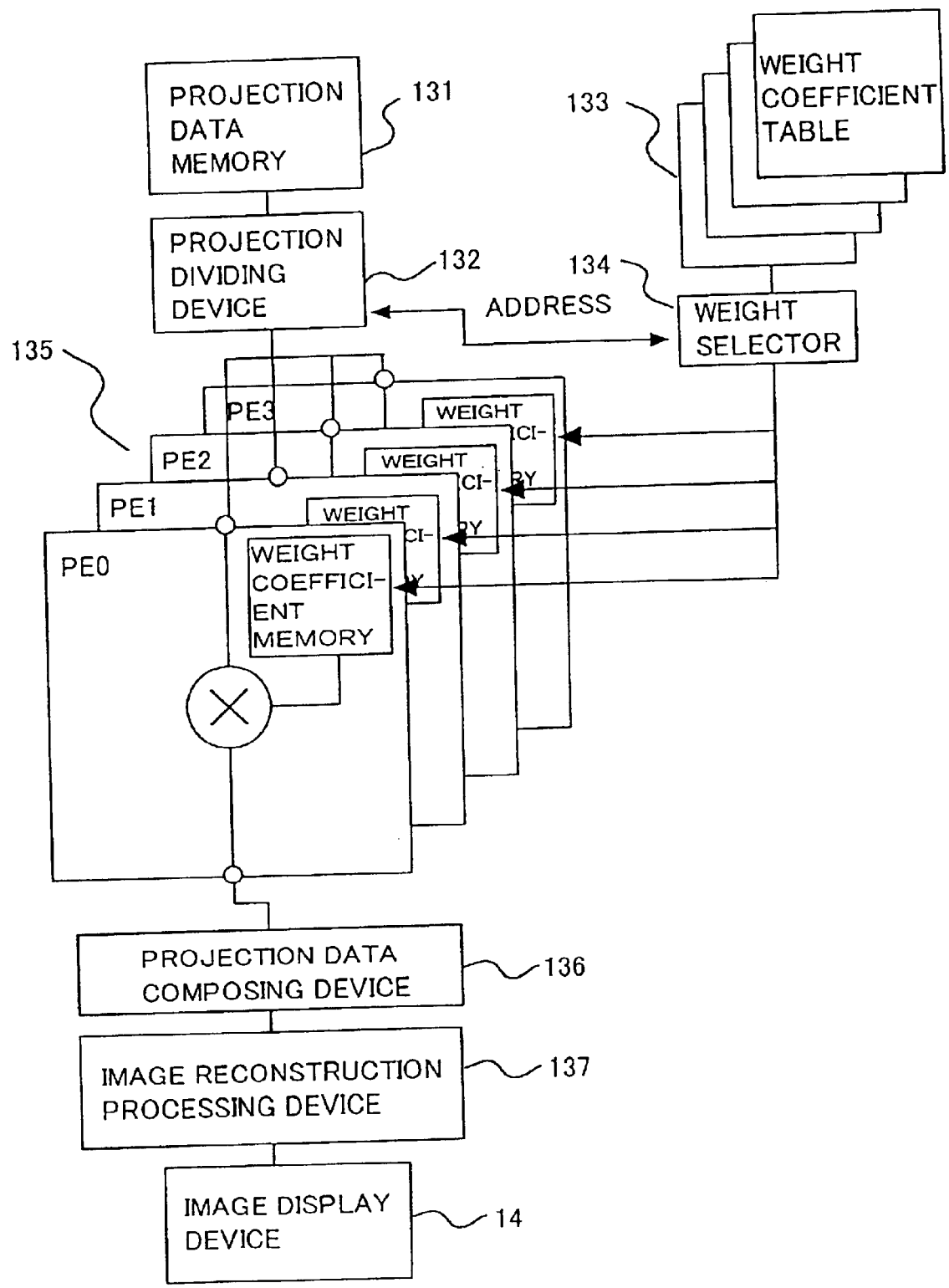
FIG. 3 is a schematic diagram showing one example of an image processing device of the X-ray CT apparatus of the present invention.

FIG. 3 is a view conceptually showing the composition of the image processing device, which comprises a projection data memory 131 for accommodating projection data of four detector rows outputted from the output selector 171 of detector 17; a projection dividing device 132 for dividing the projection data for application to each operation element; a multi-slice spiral weight generation device (hereinafter referred to simply as a weight generation device) 133 forming a weight coefficient table that stores the weight coefficients used in the operation elements for all rows of projection data; a weight selector 134 for selecting a predetermined weight coefficient table from the plural coefficient tables accommodated in the weight generation device; an operation part 135 comprised of operation elements PE0~PE3 for multiplying projection data corresponding to a weight coefficient from a selected weight coefficient table; a projection data combining device 136 for combining the operation result produced by each operation element; and an image processing device 137 for performing known image processing, such as filtered back projection, on projection data at a predetermined slice acquired by the projection data combining device 136, as well as image reconstruction.

Weight generation device 133 stores a plural number of weight coefficients, in accordance with different spiral pitches and modes or like, in the form of weight coefficient tables. The multi-slice CT apparatus of the present invention operates to apply the appropriate weight coefficient in accordance with the spiral pitch being set, when a predetermined spiral pitch is set. Weight selector 134 operates to select one weight coefficient table from the plural number of weight coefficient tables to load each operation element. In this case, not only a weight coefficient table, but also the necessary information that is suitable for the weight coefficient, for example, the gap of data at each row, with reference to a predetermined view $\beta_s$ at a predetermined slice position Zs (number of offset view), and the view length for weighting is loaded to the operation element. Hereinafter, these operations will be described.

Next, image processing will be described more particularly using correction processing of projection data at each row.

<<Generation of Multi-slice Spiral Weighting??>>

Figure 4:
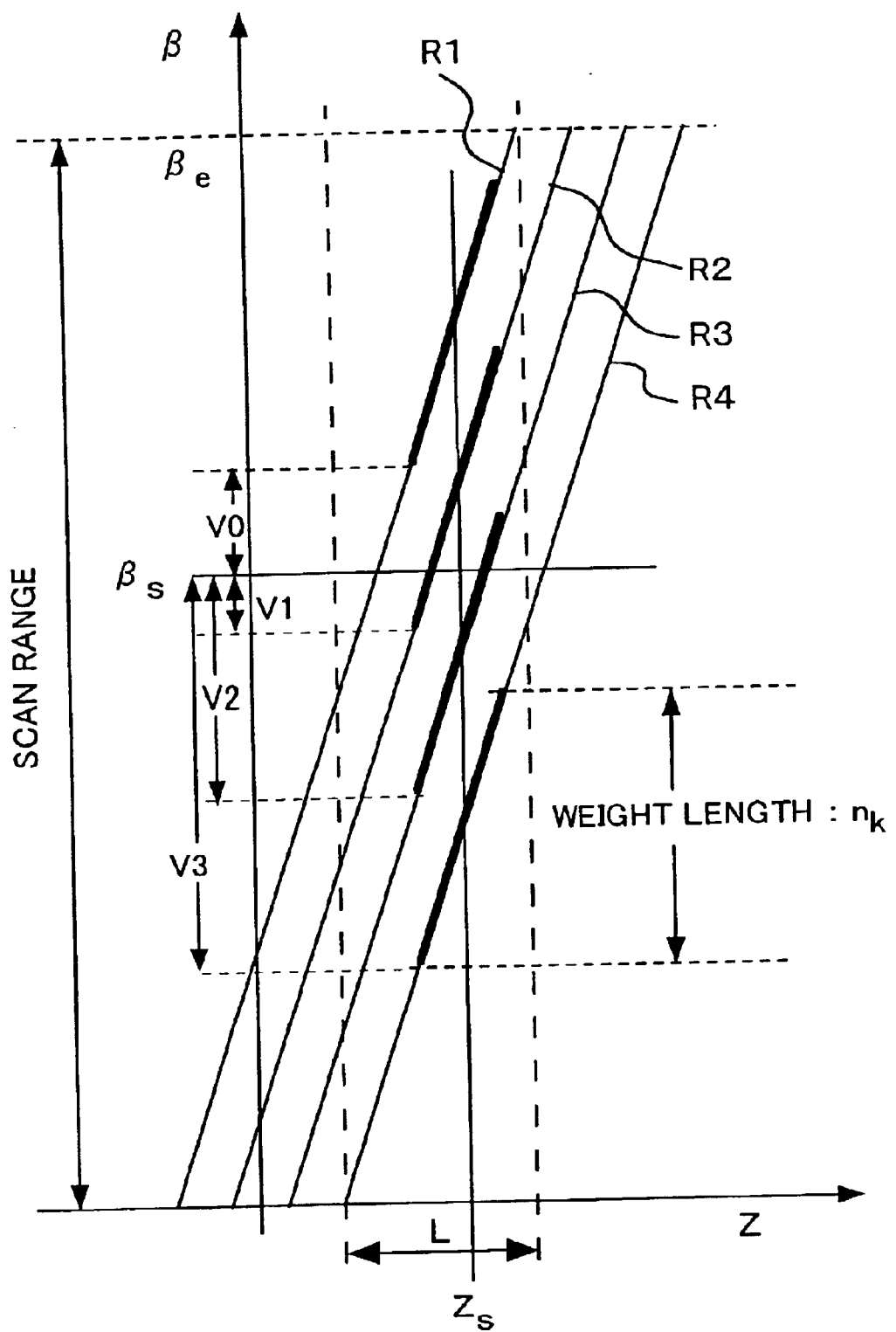
FIG. 4 is a graph illustrating spiral scan in a multi-slice CT apparatus.

FIG. 4 illustrates output data R1 to R4 of the four output system described above(hereinafter called row data) expressed on the horizontal axis as extending in the slice direction Z, the vertical axis showing the projection angle, that is to say, the focal spot of the corresponding x-rays to the angle position β. In spiral scanning, together with rotation of the scanner, each element row will differ linear relative to the slice direction. Thus, four lines are obtained along the coordinates of Z-β, as shown in the figure. To acquire projection data at a desired slice position Zs, the weight with reference to Zs (generally the weight based on the idea of interpolation) is taken advantage of for each row data. At each projection angle, the weighted data is accumulatively added to obtain projection data at one rotation about the slice.

In FIG. 4, the region indicated with a bold line on each row data represents the part for taking advantage of the weight coefficient that is not zero, that is to say, the part for adding substantially(view length: Weight Length). And, the difference V0, V1, V2, V3 between a predetermined view angle about the slice Zs (for example, the view angle when the focus point of the x-ray tube is passing) βs and the initial point of each view length at each row provide a number of offset views. These view lengths or offset view numbers are loaded as the parameter described above in the operation element, and they are used for applying a weight coefficient.

Figure 5:
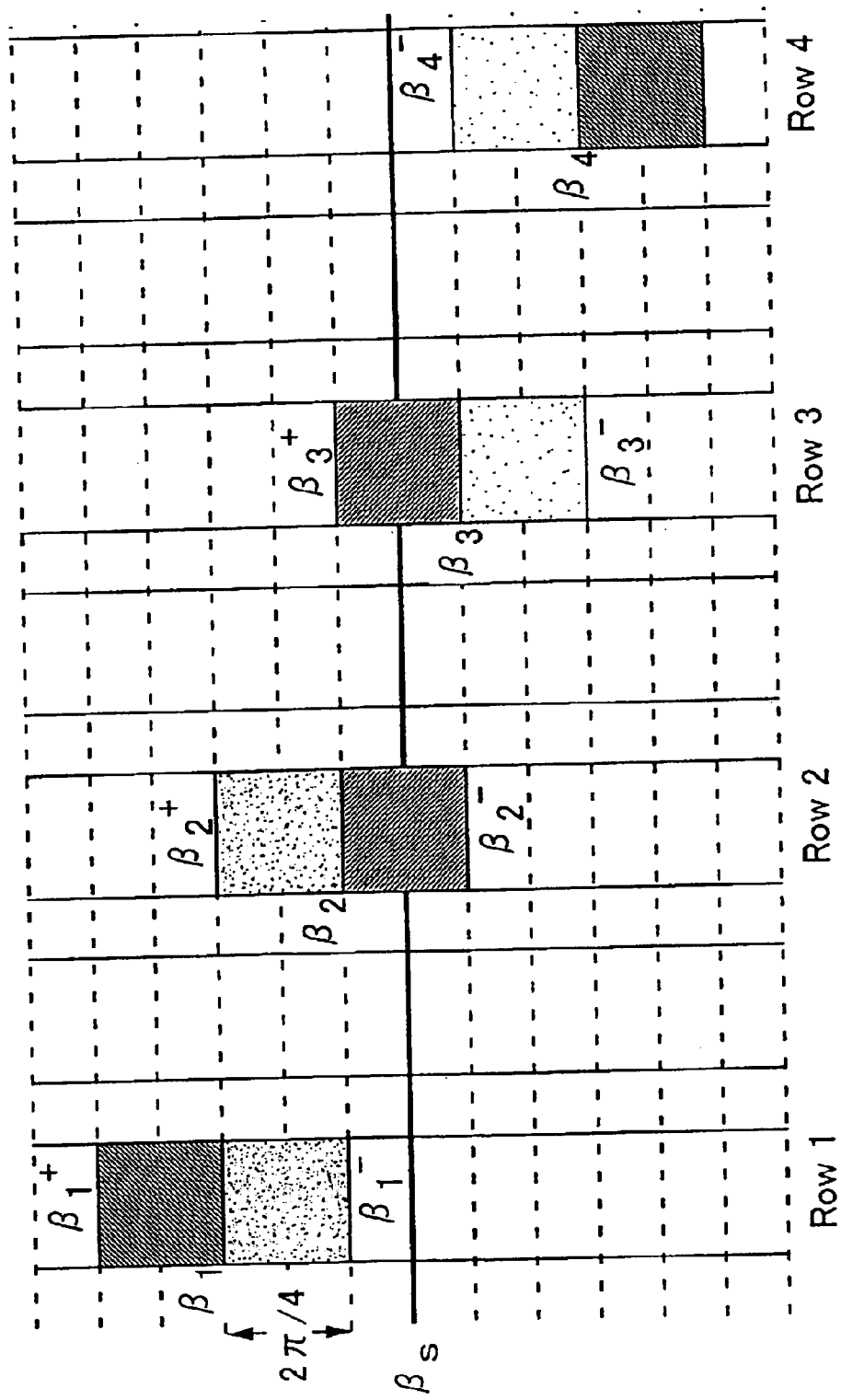
FIG. 5 is a diagram showing one example of multi-slice spiral weighting (same phase interpolation)
Figure 6A:
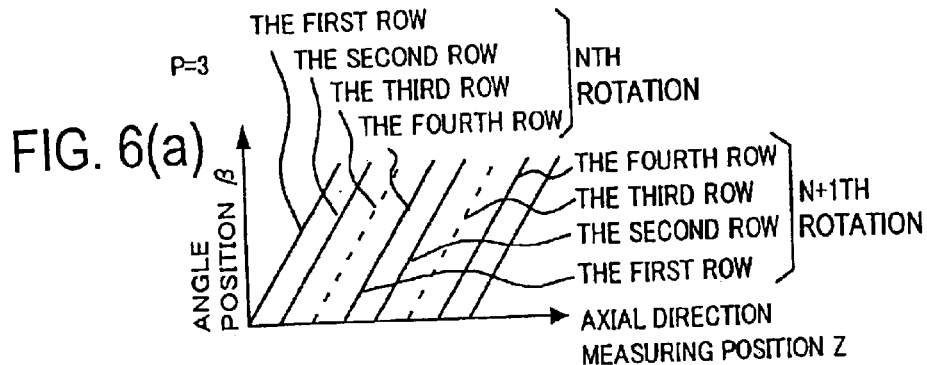
FIGS. 6(a) to 6(d) are diagrams showing the relationship between various kinds of spiral pitch and row data.
Figure 6B:
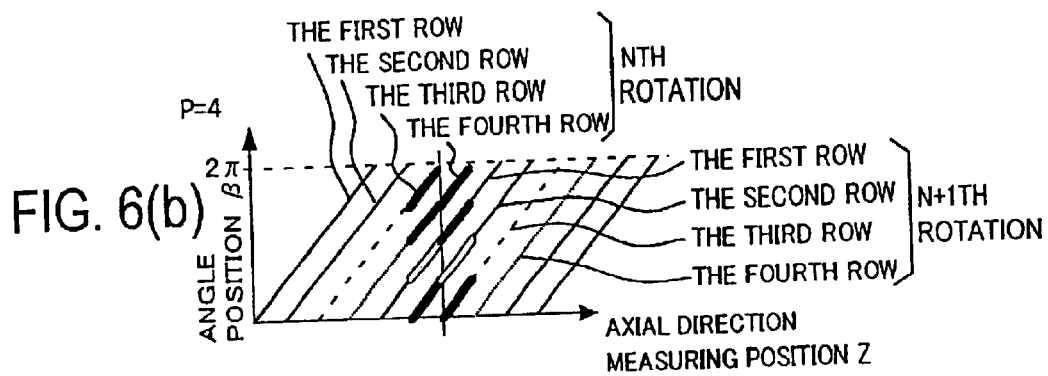

One example of the weighting applied here, as expressed on a sonogram is shown in FIG. 5. A sonogram provides a two dimensional measuring space in which the horizontal axis represents the opening angle a of a detector channel and the vertical axis represents the x-ray tube angle β (projection angle). FIG. 5 shows an example in which the detector row number is 4 and the spiral pitch P is 4. When this example is shown on the coordinate β-Z, the same as FIG. 4, the result is illustrated in FIG. 6(b). In addition, FIG. 6(a) is a example having a row number of 4, and a spiral pitch of 3. When the row number N is larger than spiral pitch P, the fourth row of period m and the first row of the next period m+1 will conflict. That is to say, overlapping rows of N–P will be generated. In this case, overlapped row datas are averaged to cope with the case of P=N. The case of P>N will be described below.

In FIG. 5, Row1 . . . Row4 correspond to projection data of the detectors in four rows. And, at each row n (n=1,2,3,4), the weighting is set with reference to the view angle (reference view angle)βn when each row n (n=1,2,3,4) passes through a predetermined slice position Zs. In the figure, the hatched region is the region for setting the weighting, and the region showing the same hatching represents a pair for interpolation. More specifically, for example, the region between β1 and β1– of Row 1 and the region between β2+ and β2 of Row 2 represent a pair. And, the region between β2 and β2– of Row 2 and the region between β3+ and β3 of Row 3 represent a pair.

Reference view angle βn is calculated according to equation (1) using view angle βs when the focus point passes through the slice Zs.

$$\beta n = \beta s + V \times \Delta\beta \times ((N-1)/2 - n + 1) \ (n=1 \ldots, N) \tag{1}$$

In this equation, V has a value of +1 or −1 in accordance with the direction of movement of the table. In addition, Δβ is a difference in view angle βn at each row, and Δβ2=π/P. In an example shown in FIG. 5, the spiral pitch P is 4, so Δβ is 2π/4.

In the region where the upper limit is βn+ and the lower limit is βn−, by making the center correspond to the view angle βn, weighting representing the Upper limit and Lower limit βn, +βn− are respectively expressed as:

$$\beta n+ = \beta + n\Delta\beta \tag{2}$$

$$\beta n- = \beta n - \Delta\beta \tag{3}$$

Specifically, weighting Wn(α,β) of row n is expressed in equations (4)~(7)

$$Wn(\alpha,\beta)=0, \text{ if } (\beta \geq \beta n+) \tag{4}$$

$$Wn(\alpha,\beta)=(\beta n+-\beta)/(\beta n+-\beta n), \text{ if } (\beta<\beta n+) \text{ AND } (\beta>\beta n) \tag{5}$$

$$Wn(\alpha,\beta)=(\beta-\beta n-)/(\beta n-\beta n-), \text{ if } (\beta>\beta n-) \text{ AND } (\beta \leq \beta n) \tag{6}$$

$$Wn(\alpha,\beta)=0, \text{ if } (\beta \leq \beta n-) \tag{7}$$

In these equations, Wn(α,β) need not necessary to be linear, as indicated by said equations. It is preferable to satisfy the following equation (8) relative to the interpolation position δ (comparison of interpolation position against sample interval):

$$f(\delta)+f(1-\delta)=1.0 \tag{8}$$

As a typical example of f (δ), $3\delta^2+2\delta^3$ is involved. In this case, Wn(α,β) corresponds to δ in the region βn−<β<βn+.

FIG. 5 illustrates the weighting in a case in which interpolation (same phase interpolation) is carried out between data for which phasing used for fan beam projection data is parallel to the α axis. But, in case of multi-slice CT, inverse phase interpolation using complementary beams having a phase which differs at 180 degrees (π) is possible, the same as 180 degree interpolation in a single slice. Complementary beams are such that, if a fan beam has a focal spot located at a position S0 ($\beta$0), as shown in FIG. 7(a), the beams are in the region of S1~S2($\beta$0+$\pi$±2$\alpha$), and they are expressed as a region having an inclination on a sonogram.

One example of weighting in a case where inverse phase interpolation is used for the complementary beams is shown in FIG. 8. Row 1~Row 3 in FIG. 8 corresponds to Row 1~Row 3 in FIG. 5. But FIG. 8 relates to a case in which the spiral pitch is P=3, and the data of Row 1 and the data of Row 4 overlap. R1', R2', R3' respectively correspond to the complementary beams of Row 3. The inverse phase interpolation is achieved with weighting relative to data in the region of ±$\Delta\beta$/2.

The difference between same phase interpolation and inverse phase interpolation for multi-slice CT will be described with reference to FIGS. 9(a) and 9(b). FIG. 9(a) shows the case of same phase interpolation. Projection data of a predetermined slice SP is the interpolation of same phase data at the nearest row, and their weight has a ramp function with SP at the maximum, as shown in the lower part of the figure. The width of this interpolating weight in the Z direction is ±$\Delta$Z. On the other hand, in the case of inverse phase interpolation, as shown in FIG. 9(b), interpolation is carried out between row data, as shown in solid line, and complementary data (dotted line), which differ in phase by $\pi$. Thus, the width of the interpolating weight in the Z direction is ±$\Delta$Z/2. In case of inverse phase interpolation, the width of the interpolating weight in the Z direction can be 1/2 compared to the case of same phase interpolation. Thus, the effective slice width can be reduced to half. And, if equation(8) is satisfied, a function other than a linear function, as shown in the figure, can be used as the weight function.

<<Variable View Interpolation>>

Thus, generally produced weighting in a multi-slice CT apparatus according to the present invention has been described. But one characteristic of the present invention is to make use of a variable view corresponding to the spiral pitch (inclination of the spiral). Now, interpolation of a variable view will be described.

At first, the concept of a variable view will be explained with reference to FIG. 7(a), FIG. 7(b) and FIG. 10. FIG. 7(a) shows the relationship between a fan beam that is parallel to the $\alpha$ axis and its complementary fan beam. FIG. 7(b) shows the relationship between a fan beam that is parallel to the $\alpha$ axis and parallel beam, in which the projection angle of each channel is equal. FIG. 10 shows the different view types on the space of a sonogram ($\alpha,\beta$). From FIG. 10, the projection angle of each line is fan beam: $\beta f = \beta$ parallelism beam: $\beta p = \beta + \alpha$ complementary fan beam: $\beta c = \beta + 2\alpha$ These beams are distinguished with respect to the inclination of the line (base line) representing the borderline of the weighting region. Thus, in multi-slice spiral weighting according to the present embodiment, a reference line of each row can be selected according to the following equation.

$\beta n+ = \beta n + \Delta\beta + M\alpha \beta n- + \beta n - \Delta\beta + M\alpha$, M=0,1,2 reference line of M=0 is a parallel beam, M=1 is a parallel beam, and M=2 is a complementary beam, that is to say, a fan beam. In the example of FIG. 5, the case of M=0 is shown, thus the reference line is a fan beam. Therefore, this example represents a case of same phase interpolation between fan beam projection data.

Figure 11:
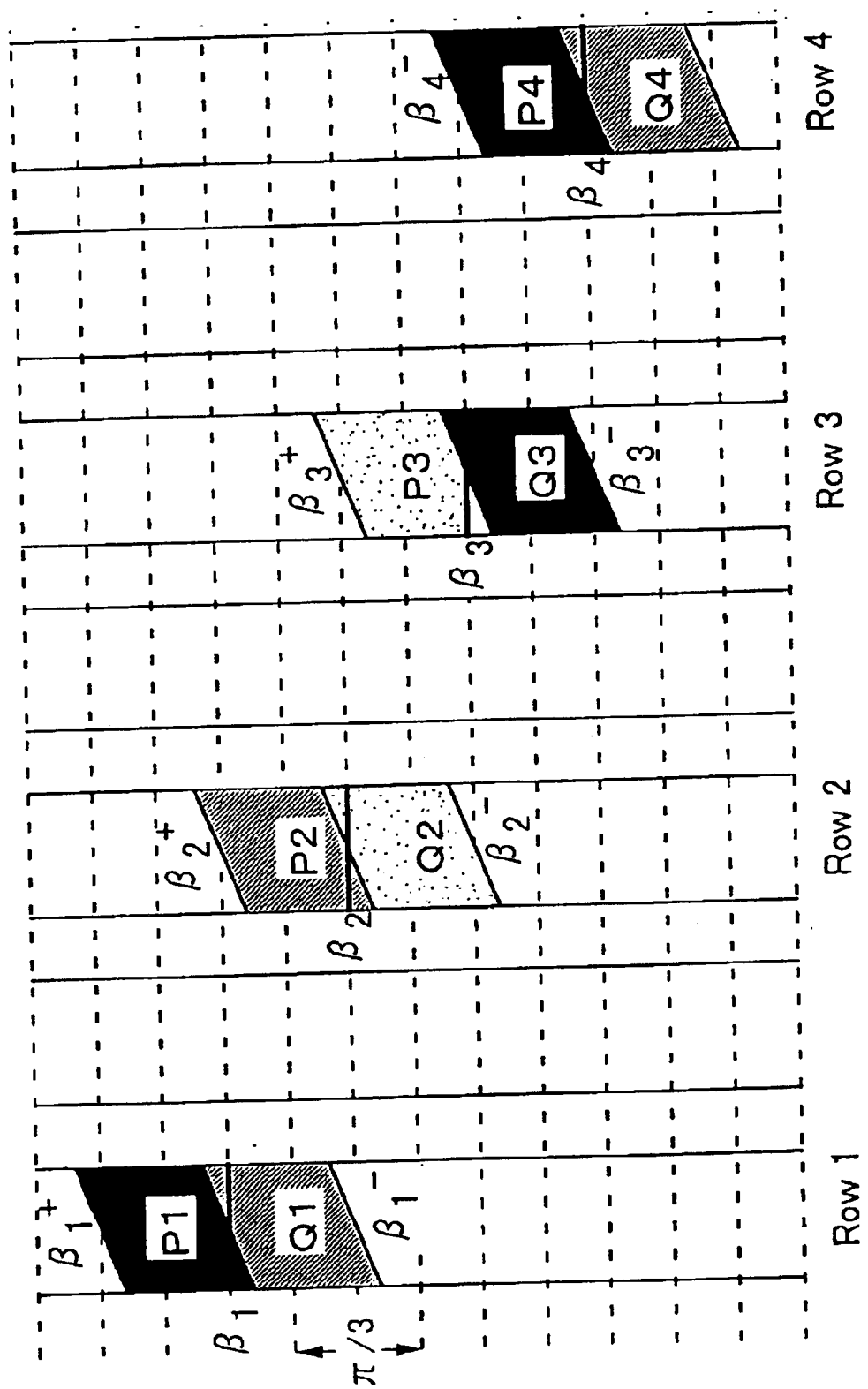
FIG. 11 is a diagram showing one example of weighting using a variableness view (M=1) according to the present invention.

The case of M=1 is shown in FIG. 11. In this case, the reference line is a parallel beam. Each region has a parallel beam data set having a spread of $\Delta\beta$. Therefore, weighting corresponding to same phase interpolation between parallel beam projection data is performed. In the case of M=2, as shown in FIG. 7(a), 4 $\alpha$m is the inclination, and weighting corresponding to same phase interpolation between fan beam and complementary beam projection data is performed. In a case other than M=0, the reference line inclines relative to the slice position, and so this is not a problem clinically.

The view type (M) generally will change in accordance with the spiral pitch (table transmitting amount). By making the inclination of the spiral and the inclination of the beam close to each other, the image becomes high quality because data used for interpolation is close to the actual measuring position. Selection of M can be coupled to the inclination of the spiral. It is possible to effect arbitrary selection comprising an exclusive mode, respectively.

Now, the case of same phase interpolation will be described with reference to FIG. 11. But the concept of variable view can be applied in the same manner as the case of inverse phase interpolation. The description is directed to setting of a variable view corresponding to the spiral pitch as one embodiment of multi-slice spiral weighting generation.

Figure 12:
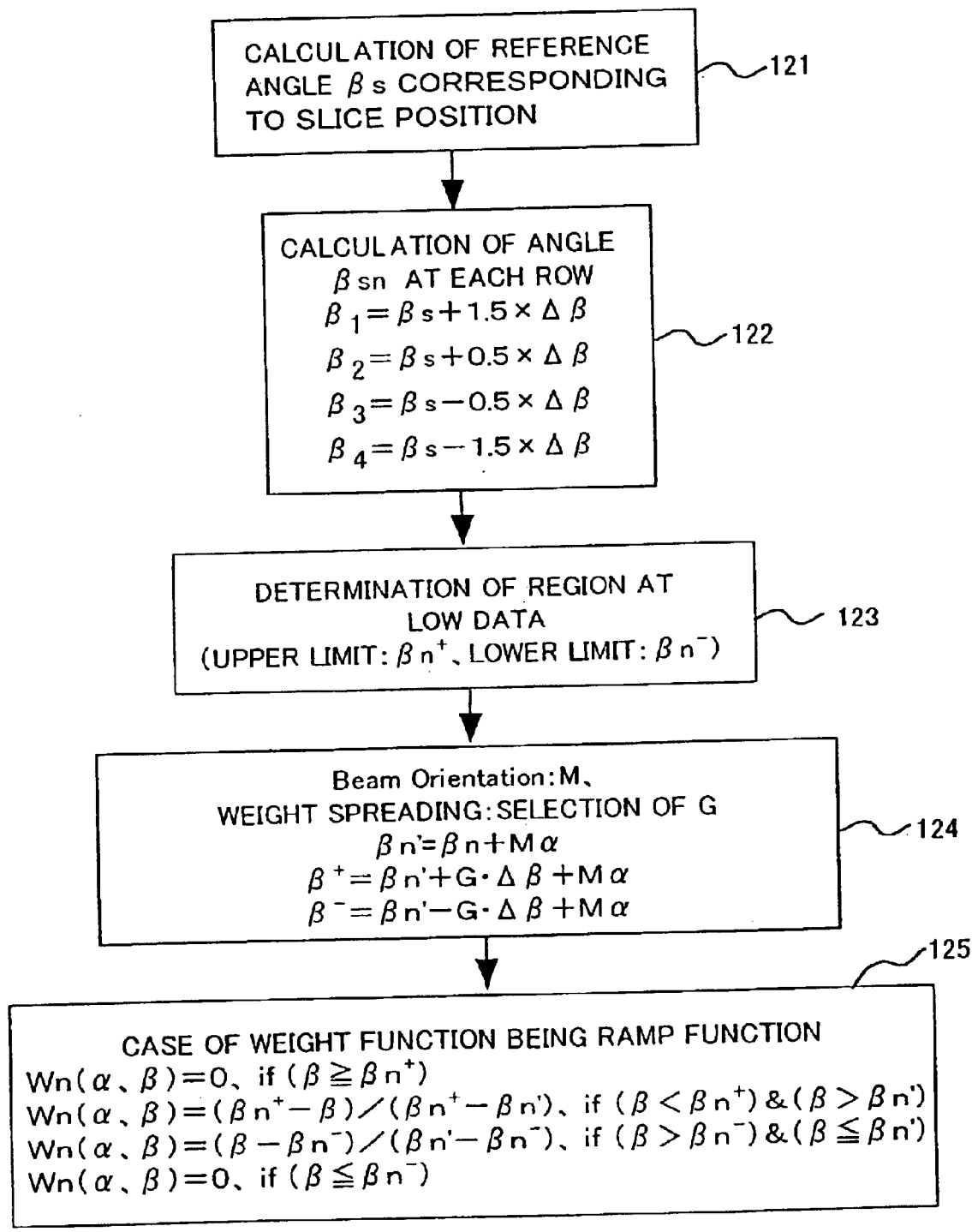
FIG. 12 is a diagram showing the flow of weight generation processing according to the present invention.
Figure 13:
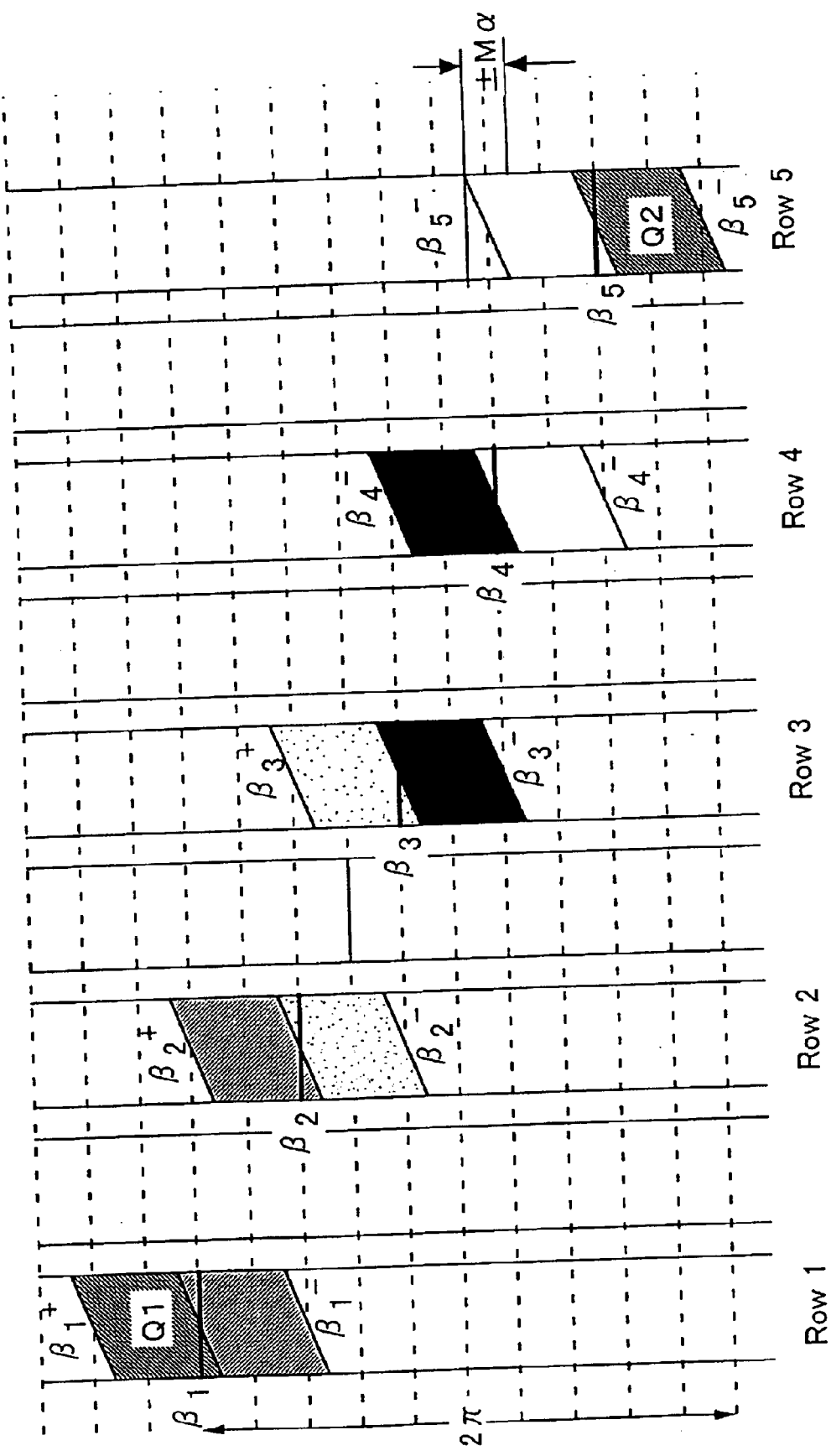
FIG. 13 is a diagram showing one example of weighting using a virtual detector according to the present invention.

The flow of weighting generation in one row is shown in FIG. 12. The generation of weighting is achieved with a weighting generation device 133 in the image processing device 13, as shown in FIG. 13. At first, the reference angle $\beta$s is calculated corresponding to the slice position for image reconstruction (step 121). Reference angle $\beta$s is the view angle, for example, when the focal spot passes through slice Zs. Then, from equation (1), reference angle $\beta$n at each row is calculated (step 122). Moreover, the upper limit $\beta$n+ and the lower limit $\beta$n− of the weighting region of row data is determined based on the M value that was previously selected or previously set (step 123). Furthermore, an expanse of weighting (range of weighting) is set (step 124). In FIG. 12, G represents the parameter for controlling the weighting width. As will be described later, the multi-slice spiral weight according to the present invention can be varied in an arbitrary spread of weighting in accordance with the image slice thickness. After that, for example, the ramp function as expressed in equations (4)~(7) is applied to determine the weight Wn (step 125).

<<Setting of Virtual Detector>>

Figure 6C:
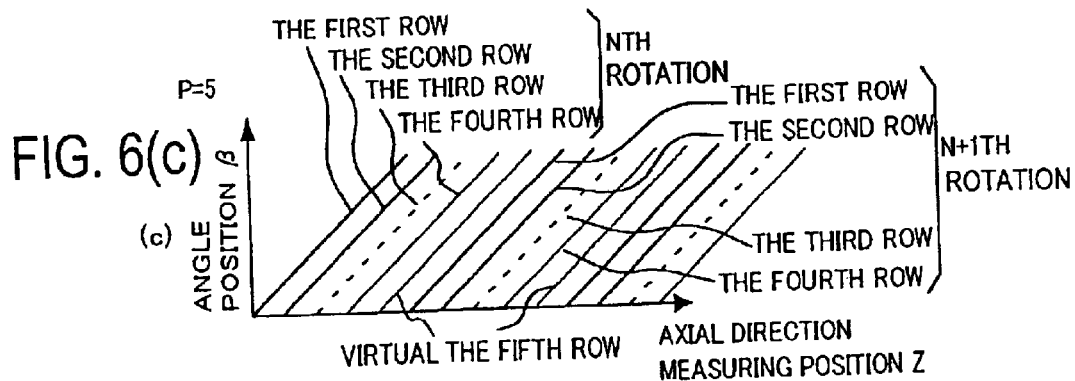
Figure 6D:
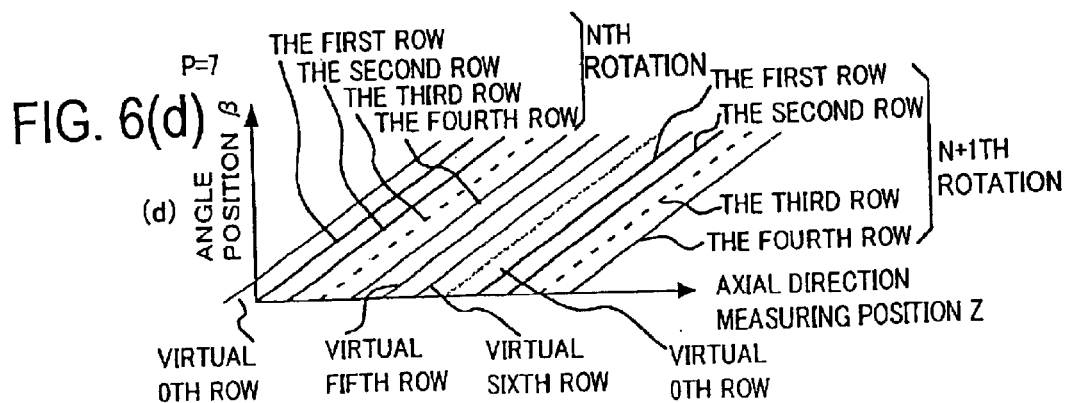

Next, as a second embodiment, the setting of a virtual detector corresponding to the spiral pitch and generation of weighting about all row data comprising them will be described. In the example shown in FIG. 5, a row number N and spiral pitch P having a relation N≧P is illustrated (FIGS. 6(a), 6(b)). But, when P>N, as shown in FIGS. 6(c), 6(d), K(=N−P)<0. Thus, the data of K rows is shortened. To achieve the same phase interpolation, N≧P is conditioned. Then, a row serving as a virtual detector row is virtually set according to the present embodiment. For example, by measuring with a pitch 5 of a five row multi-slice system, correction can be easy to perform, and ideal measurement is possible.

FIG. 13 shows the case of pitch 5 in a 4 row multi-slice system. The fifth row set here actually does not exist. So, for example, they can be calculated from Row 3, Row 4 with extrapolation and substituted with the fifth row complementary beam. Weighting is applied for them.

Figure 14:
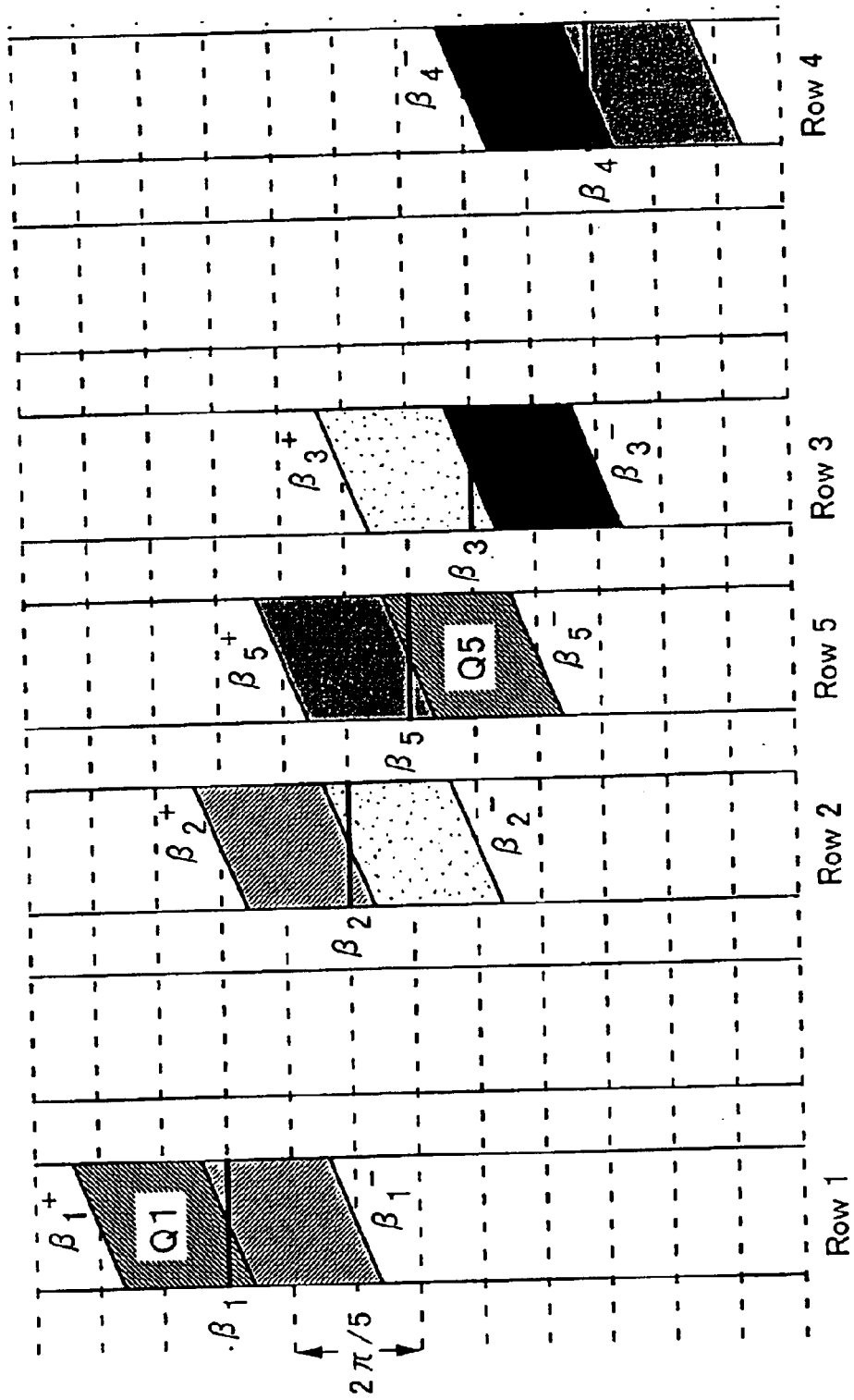
FIG. 14 is a diagram showing another example of weighting using a virtual detector according to the present invention.

FIG. 14 shows an example in a case applied to a complementary beam. Complementary data is the data of a half period phase difference ($\pi$). Thus, from the relationship of $\pi=\Delta\beta\alpha\times P/2$, data will differ at the 2. 5 row when P=5. That is to say, complementary data of the fifth row can be treated as a row with interpolation from Row 2 and Row 3. In this case, regions shown with the same hatching in the figure have the pair of interpolation(for example Q1 in Row 1 and Q5 in Row 5), but data corresponding to the fifth row does not actually need to be calculated. It is possible to simply divide the weight of the virtual detector to the actual detector in accordance with the interpolation weighting for the case in which the data of the virtual detector is simply calculated. For example, in case is performed from Row 2 and Row 3, Row 2 and Row3 are divided to 0.5 each.

$$W2(\alpha,\beta)=W2(\alpha,\beta)+0.5*W5(\alpha,\beta)$$

$$W3(\alpha,\beta)=W3(\alpha,\beta)+0.5*W5(\alpha,\beta)$$

In this case, the operation for calculating the data of the fifth row is not necessary. Thus, the operating time can be reduced, and it is practical. And, when restriction of processing time does not need to be considered, it is preferable to calculate the row data of the virtual detector with the operation, and weighting based on equations (4)~(7) can be applied to them. In either case, introduction of the concept of a virtual detector makes it possible to correct easily and achieve ideal measurement.

In addition, FIG. 13 and FIG. 14 show weighting applied in the case M=1 is selected as a variable view, that is to say, in case interpolation between parallel beam projection data is performed. Accordingly, the complementary beam of the fifth row is also the parallel beam. The present embodiment can also be applied to the case in which a fan beam is used.

Figure 15:
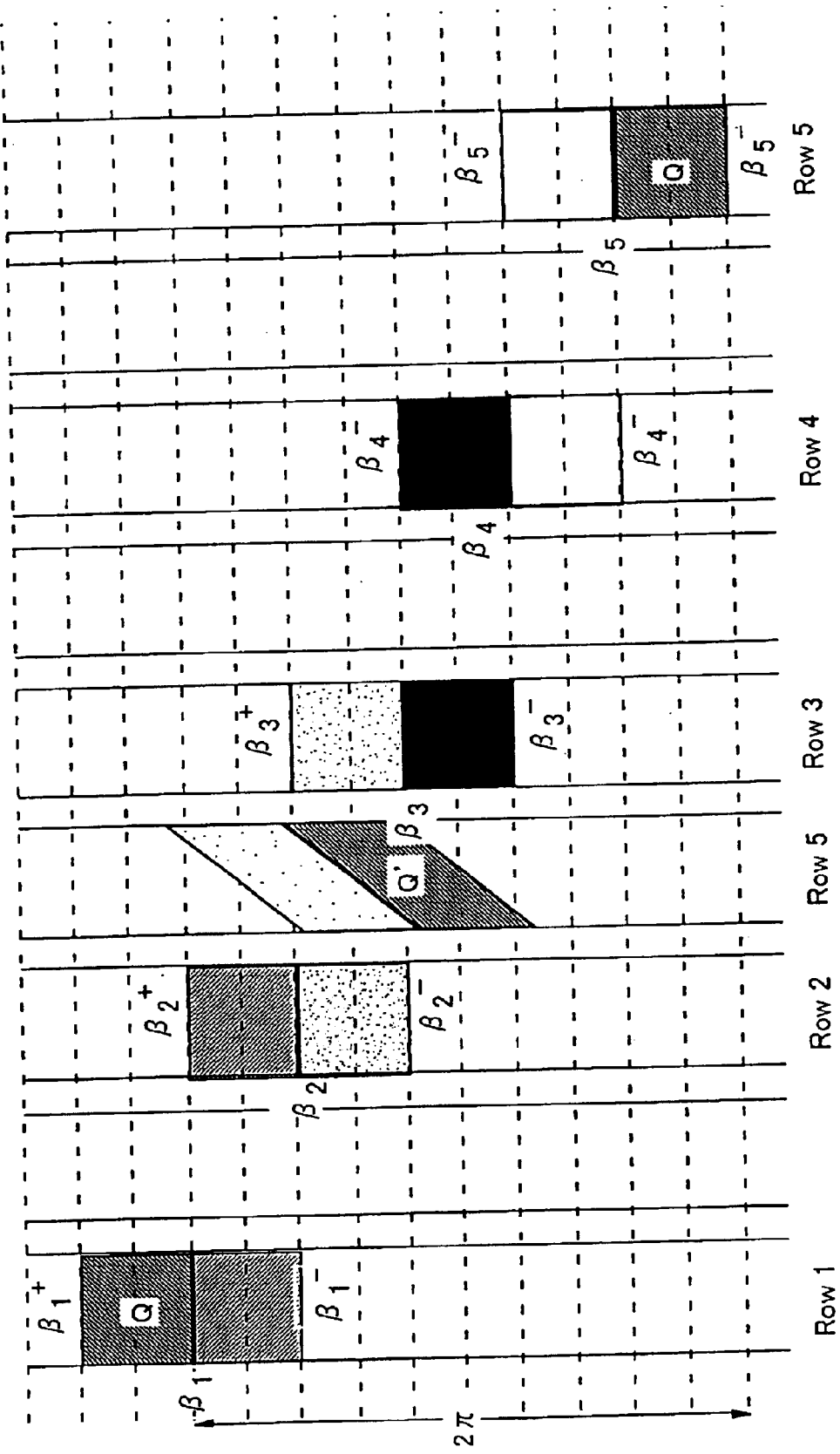
FIG. 15 is a diagram showing another example of weighting using a virtual detector according to the present invention.

FIG. 15 shows setting and weighting of a virtual detector when a fan beam is used (spiral pitch P=5,M=0). In this example, when a complementary beam is used as the data in the fifth row of the virtual detector, complementary data is the complementary fan beam of M=2, as shown in the figure. Region Q is used instead of region Q'. Setting of the weight about the complementary beam is similar to the case of FIG. 14.

Figure 16:
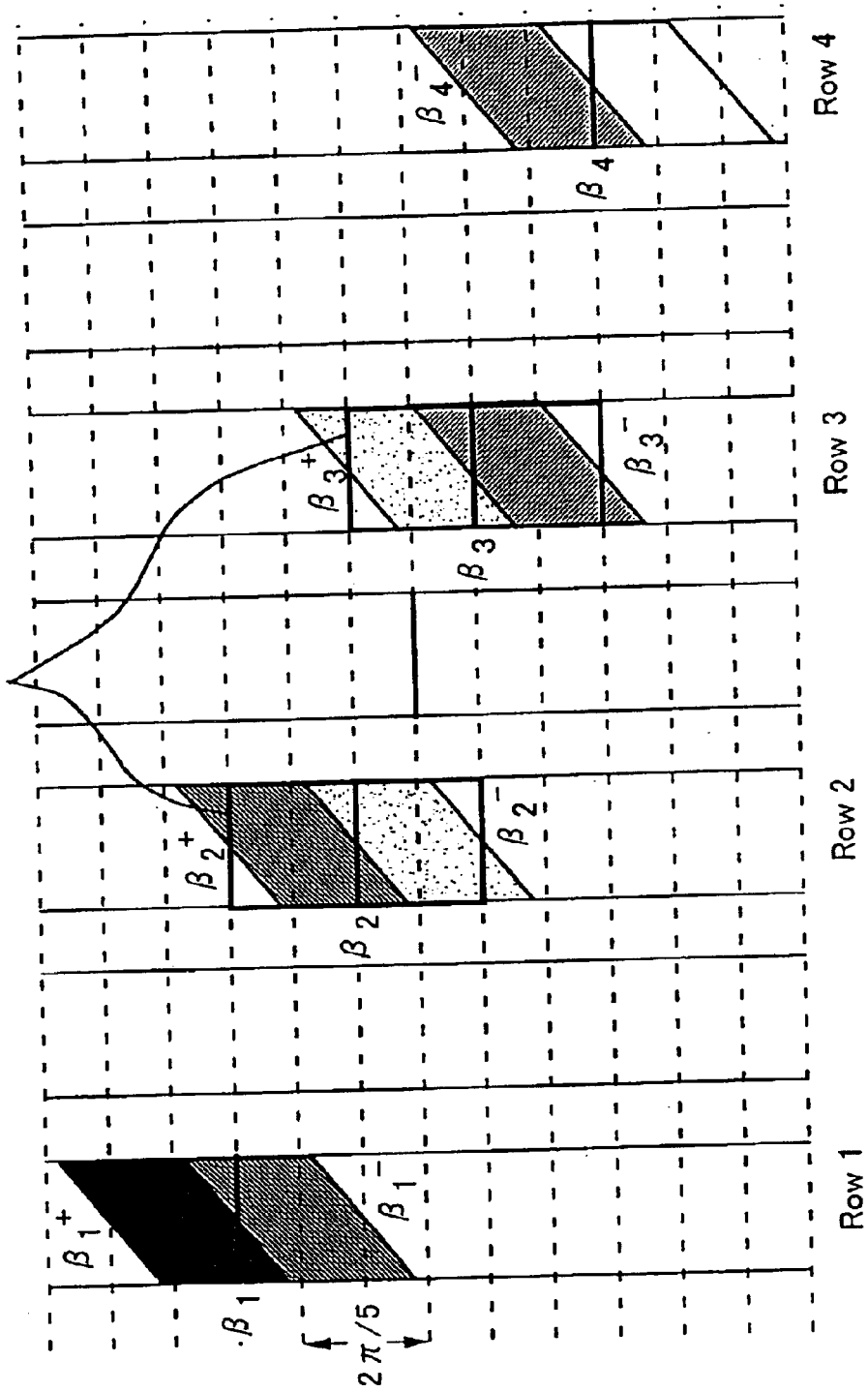
FIG. 16 is a diagram showing another example of weighting using a virtual detector according to the present invention.

In FIG. 14, the difference between the spiral pitch and row number equals 1 is shown. When it is more than two, it can be similarly applied. FIG. 16 shows an example in which the spiral pitch P equals 6, and M=2. When the spiral pitch is 6, K=2(=6−4). So, two rows of virtual detectors(0 row or 5 row) are set. In this case, a complementary data set of virtual detectors have a phase difference about three rows. Data of the virtual 0 row is the third row, and data of the virtual 5 row can be compensated with the second row. The region corresponding to these virtual rows is shown with only a thick frame without hatching. In this case, the complementary fan beam of the virtual row fan beam having M=2 is a M=0 fan beam.

This embodiment includes not only the case where the spiral pitch is an integer, but also the case where the spiral pitch comprises a fraction. In this case, the array of detectors can be further subdivided. For example, in case of 4 rows and a pitch of 4. 25, 16 rows and a pitch of 17 are composed for the weighting. When these detector arrays are subdivided as thus described, the problem can be simplified, and the concept of a virtual array can be applied easily.

<<Inverse Phase Interpolation>>

Figure 17A:
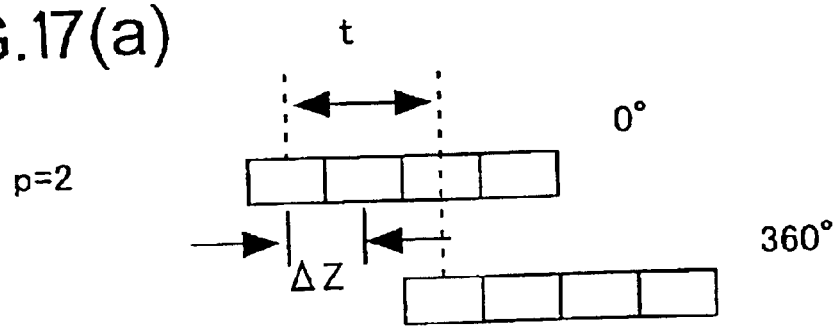
FIGS. 17(a) to 17(c) are diagrams showing the relationship of complementary data between a real detector and a virtual detector.
Figure 17B:
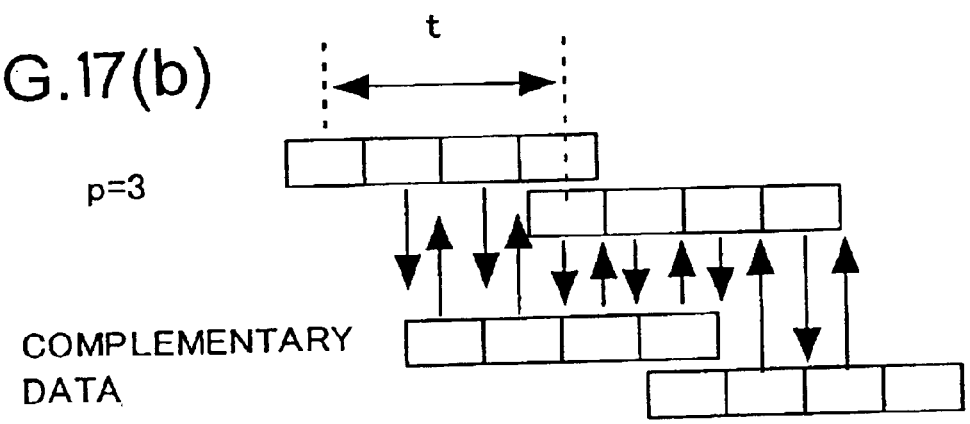
Figure 17C:
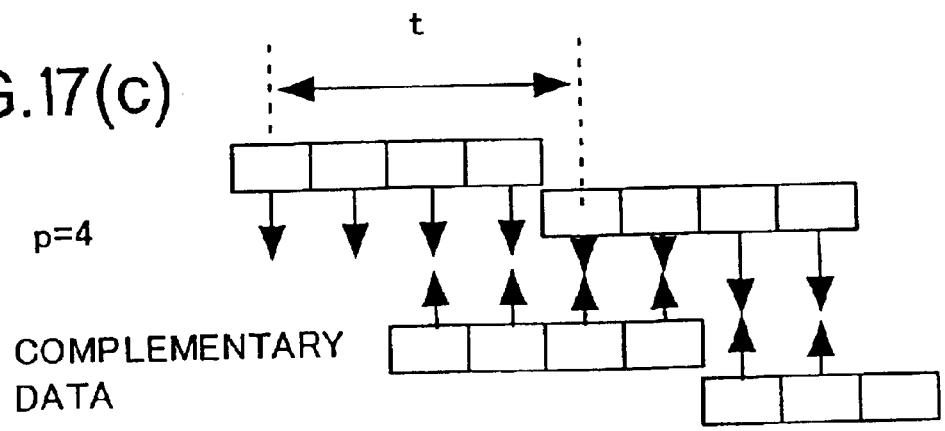

The concept of using a virtual detector can be applied to inverse phase interpolation as well. But, inverse phase interpolation is effective in the case of an odd number pitch. That is to say, as shown from a comparison between FIG. 15 and FIG. 16, when the spiral pitch is an odd number, the complementary data of the virtual detector rows is positioned intermediate between data of actual detector rows. On the other hand, when the spiral pitch is an even number, the complementary data of the virtual detector is that of an actual detector row. In this case, the effect of high resolution described in FIG. 9 can not be expected. This is illustrated in FIGS. 17(a) to 17(c).

Figure 18:
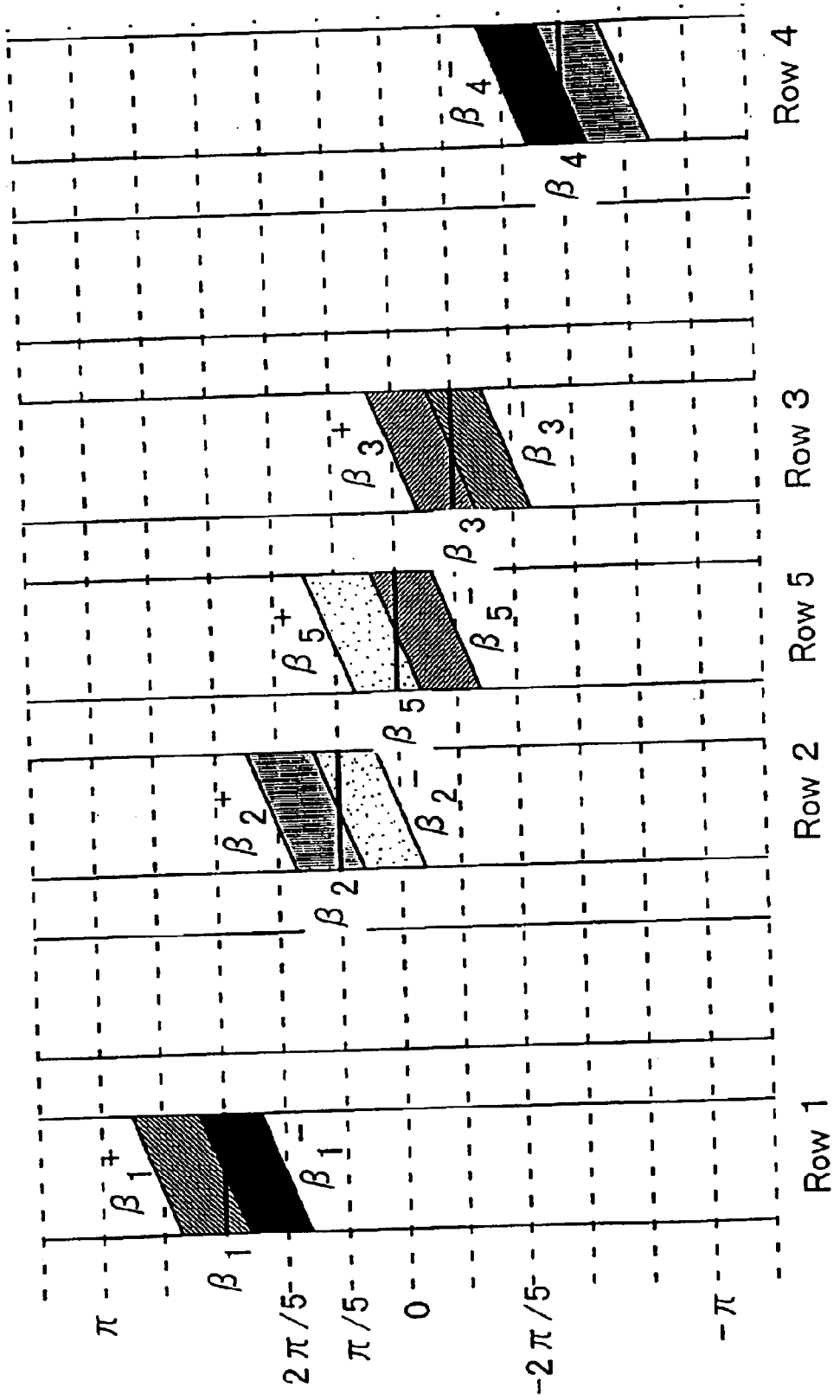
FIG. 18 is a diagram showing weighting using a virtual detector (the case of inverse phase interpolation)

Accordingly, in case of an odd number, an ideal data distribution can be performed using a virtual detector. Inverse phase interpolation can easily be performed to achieve the desired effectability. FIG. 18 shows an example of inverse phase interpolation for the case in which a virtual detector is set in Row 5. As thus described, in case of an odd pitch number, inverse phase interpolation can be achieved with a weighting width formed with the same phase interpolation to be $\Delta\beta/2$. And, a more than 20% higher resolution is made possible. But, in case of P=3<N, interpolation of the actual detector is possible without using the virtual detector as shown in FIG. 8. R1'~R3' in FIG. 8 exists in data Row 1~Row 3 of the actual detector.

The complementary data set for compensating the virtual detector is, for example, when the reference line is $\beta n'=\beta n+M\alpha$, $\beta n'=\beta n \pi+(2-M)\alpha$, because the phase differs about $\pi$ and the slope is (2−M). The division line of this complementary data set is expressed as a pair of interpolation. So, the parallel beam (M=1) is paired with a parallel beam, and the fan beam is paired with a fan beam or a complementary beam.

<<High Dimensional Interpolation>>

The above-mentioned example was directed to a case wherein the weighting width is $\Delta\beta$ fundamental and the most high resolution able odd pitch is $\Delta\beta/2$. But, it is possible to modify the weighting width arbitrarily as a minimum to be $\Delta\beta/2$. With changing of this width, the effective slice width of the image can be arbitrarily modified.

In case the width of the weighting is arbitrarily modified, a plural number of weighting, which differ in weight width, is weight averaged to produce a new weighting. For example, weighting Wa of width $2\Delta\beta$ and weight Wb of width $\Delta\beta$ are used for weight averaging. Or, said interpolation position is already determined ($\delta$ in equation (8)), so high dimensional interpolation is possible.

<<Canceling of Discontinuity>>

Figure 19:
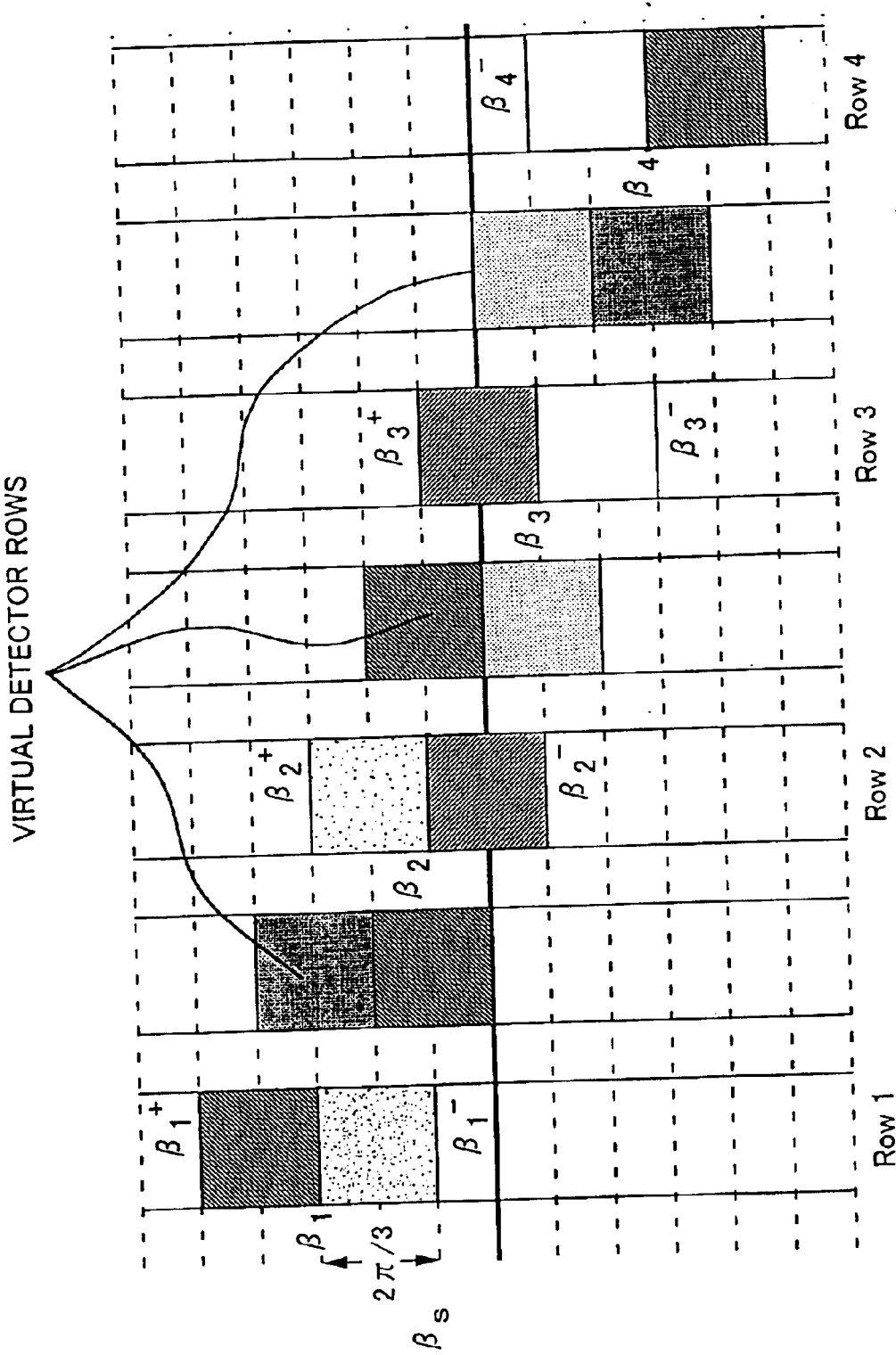
FIG. 19 is a diagram illustrating the setting of a virtual detector for canceling a discontinuity.

As thus described, in multi-slice spiral interpolation, pair of interpolations differ at each $\Delta\beta$. With such changing, discontinuity, is generated in projection data after correction. This discontinuity is outstanding the when width of the weighting is small. Thus, in this embodiment, a virtual detector VR is located between each row, as shown in FIG. 19. Weighting is set at all rows comprising this virtual detector. Thus, for example spiral projection data obtained with row 4, spiral pitch 3, is the same as row 8 or row 7, spiral pitch 8. Weighting relative to the virtual detector VR is applied to weighting in the case of row 3 and pitch 4 considering only the virtual detector. Weighting relative to this virtual detector is divided according to the surrounding weight. Weighting of each row is added.

As thus described, assuming that a virtual detector is located between such actual detector, weighting is set considering the whole row comprising a virtual detector, and the discontinuity is cancelled with application to each row data. Thus, it is possible to achieve high image quality in multi slice spiral scanning.

In FIG. 19, the case of the spiral pitch being an integer (=3) is illustrated. But, in this embodiment, the use of a fractional spiral pitch is also effective. For example, the case of four rows, with a spiral pitch of 1. 25, can be accommodated with 8 rows, and a spiral pitch of 2. 5. In such an arbitrary spiral pitch, using the concept of a virtual detector, effective setting of the weighting is possible.

Figure 20:
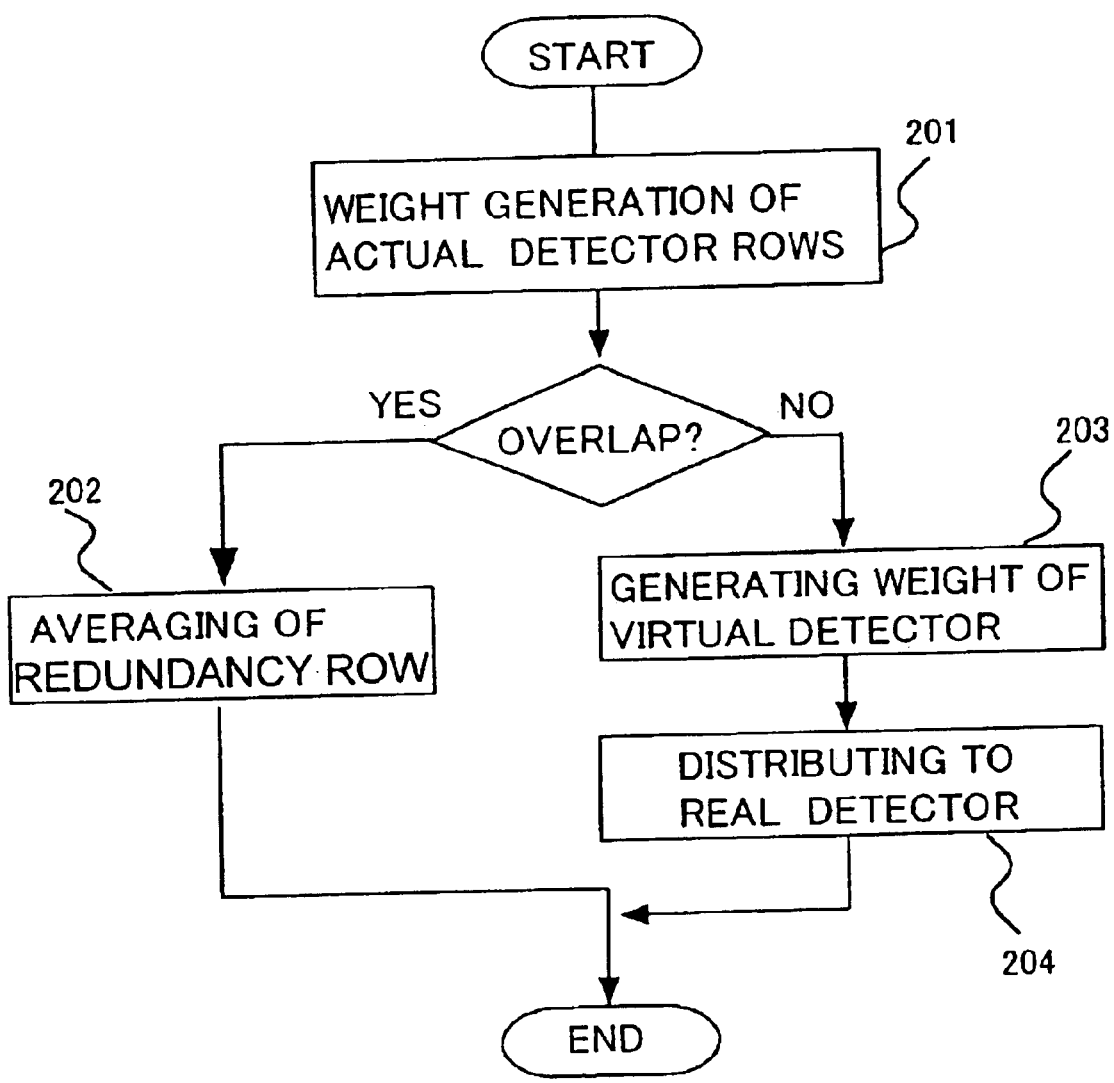
FIG. 20 is a diagram showing the flow of weight generation processing in a case in which a virtual detector is set.

The flow of weight generation in the case of a virtual detector being used is shown in FIG. 20. As shown in the figure, at first, weighting about an actual detector row is generated (step 201). In case the row number N satisfies P<N, overlapping of about N–P rows results. In this case, a row for overlapping is averaged to avoid redundancy (step 202). On the other hand, a virtual detector is employed when the row number lacks in the case of N<P, and the weighting is generated(step 203). This weighting is divided to weighting of the actual detector (step 204). In addition, in case a virtual detector is set for canceling a discontinuity, as thus described, after distributing the weighting set to a virtual detector based on real detectors in the neighborhood, said weighting processing is performed at step 201.

<<Collimate Control Means>>

In the explanation described above, when the row number N is larger than the spiral pitch P, the rows of N–P for overlapping are averaged to avoid redundancy. However, it is preferable to adjust the number of rows from the viewpoint of reducing the x-ray dose applied to a patient.

Figure 21B:
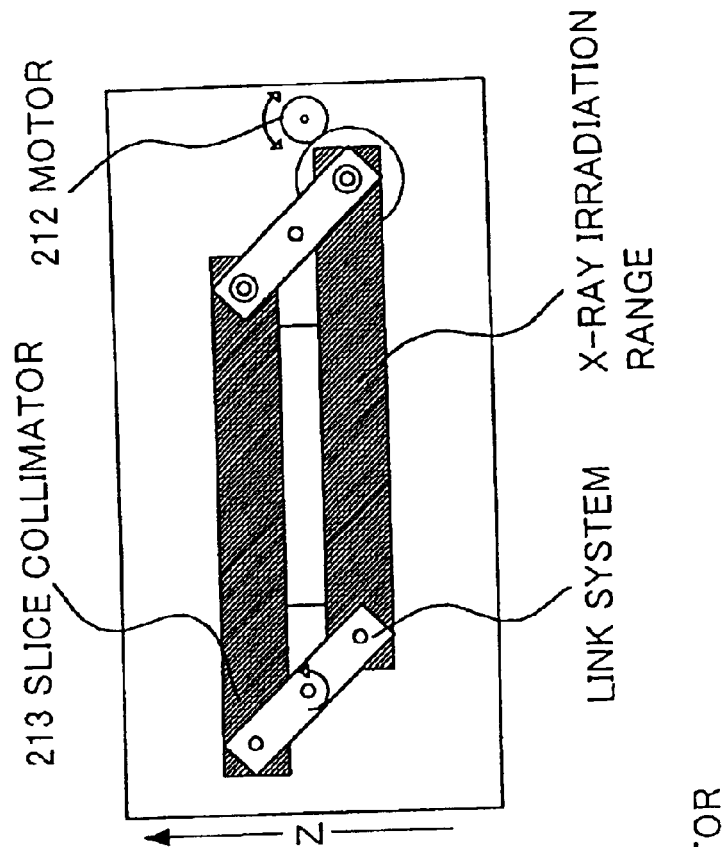
FIGS. 21(a) and 21(b) are diagrams showing one example of a system for controlling the row number of detectors.
Figure 21A:
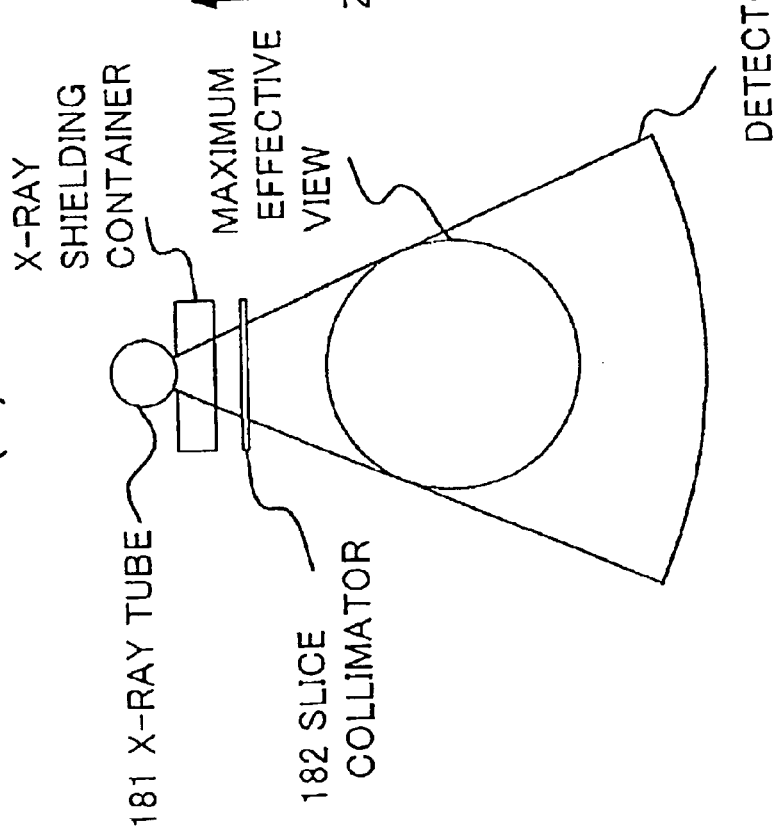

In a further another embodiment of the invention, a system for adjusting the width in the slice direction of the x-rays is incorporated in collimator 182 for controlling the width of the x-rays and the opening angle. This system is shown in FIGS. 21(a) and 21(b). This adjusting system is comprised of control means 211 (FIG. 2) controlled in response to a command from host computer 16 (FIG. 1), a motor 212 for driving slice collimator 213 in the form of a link system, and means for communicating rotation of the motor 212 to the link system of the slice collimator 213. When information of the essential row number corresponding to the spiral pitch from host computer or information corresponding to it is given to control means 211, control means 211 operates to adjust the slice direction aperture of the slice collimator using driving motor 212. For example, with rotation of motor 212, when the link is rotated in a clockwise direction as seen in the figure, the x-ray irradiation range is spread in the Z direction. And, when it is rotated in a counterclockwise direction, the x-ray irradiation range is narrowed in the Z direction. The irradiating region in the direction perpendicular to the Z direction is restricted by an x-ray shielding container.

This adjusting system is effective especially when the row number of detectors is increased to 16~96 rows. Basically when the row numbers are about half of the pitch P, a perfect image can be reconstructed. In the collimator shown in the figure, a link system is adopted. But, when a system is employed in which the width in the Z direction is adjustable, for example, a known system such as a slide system can be adopted.

By providing a system for the controlling the row number in a multi-slice CT system, adjustment of the row number in relation to said weighting algorithm is possible. Thus, interpolation processes of the present invention can be effectively improved, and with elimination of the redundancy of measurement, the x-ray dose applied to the patient can be reduced.

According to the present invention, setting of appropriate interpolated weighting is possible in accordance with the spiral pitch in a multi-slice CT system, so high image quality can be obtained. And, the present invention involves the concept of a virtual detector. Thus, the appropriate interpolation weight can be effectively set in various cases of the relationship between the detector row number and the spiral pitch. Therefore, it is possible to cancel a discontinuity generated in multi-slice spiral weighting. Furthermore, according to the present invention, redundant measurement can be made small, and the x-ray dose applied to a patient can be reduced.

What is claimed is:

1. A multislice CT apparatus comprising:

a detector including a plural number of detector elements arranged in an axial direction of the multislice CT apparatus;

a moving table on which an object to be examined is placed to be examined with a rotating X-ray source and at least ones of the plural number of detector elements, to acquire a plural number of spiral projection data;

a correction processing means for performing correction processes to the spiral projection data; and an image reconstruction means for reconstructing a tomographic image from corrected spiral projection data;

wherein the correction processing means has a weighting coefficient table storing a plural number of predetermined different multislice spiral weighting coefficients corresponding to predetermined ones of spiral pitch of a table moving amount at rotation against a row interval of the detector, and selects one of the plural number of predetermined different multislice spiral weighting coefficients in accordance with a predetermined spiral pitch at measurement for applying weighting to the spiral projection data of each row, and combines the spiral projection data after applying weighting application to each detector element row.

2. A multislice X-ray CT apparatus as claimed in claim 1, in which the correction processing means changes a weighting region of spiral projection data in accordance with the predetermined spiral pitch at measurement.

3. A multislice X-ray CT apparatus as claimed in claim 1, in which the correction processing means comprises a plurality of weighting processing means for performing weighting processing for differing rows in parallel, with each weighting processing means including a weight coefficient memory to store a multislice spiral weighting coefficient selected from the weighting coefficient table, for a subject row to be processed.

4. A multislice X-ray CT apparatus as claimed in claim 1, in which the correction processing means generates the predetermined different multislice spiral weighting coefficients of the weighting coefficient table for each row by:

calculating a reference angle $\beta s$ corresponding to a slice position for image reconstruction;

calculating a reference angle $\beta n$ at each row;

calculating an upper limit $\beta n^+$ and a lower limit $\beta n^-$ based on a preset value M;

selecting a parameter G for controlling a weighting width, and calculating a range of weighting; and applying at least one predetermined function to determine weighting Wn.

5. A multislice X-ray CT apparatus as claimed in claim 4, wherein at least one of:

the calculating of the reference angle $\beta n$ at each row uses the equations:

$\beta 1 = \beta s + 1.5 \times \Delta \beta,$ $\beta 2 = \beta s + 0.5 \times \Delta \beta,$ $\beta 3 = \beta s - 0.5 \times \Delta \beta,$ $\beta 4 = \beta s - 1.5 \times \Delta \beta;$ the calculating of the an upper limit βn⁺ and the lower limit βn⁻ uses the equations:

$\beta n^+ = \beta n + \Delta \beta,$ $\beta n^- = \beta n - \Delta \beta;$ the calculating of the range of weighting uses the equations:

$\beta n' = \beta n + M\alpha,$ $\beta^+ = \beta n' + G \cdot \Delta \beta + M\alpha,$ $\beta^- = \beta n' - G \cdot \Delta \beta + M\alpha;$ and the applying of the at least one predetermined function to determine the weighting Wn uses the equations:

$Wn(\alpha, \beta) = 0$, if $(\beta \geq \beta n^+)$, $Wn(\alpha, \beta) = (\beta n^+ - \beta)/(\beta n^+ - \beta n')$, if $(\beta < \beta n^+)$ AND $(\beta > \beta n')$, $Wn(\alpha, \beta) = (\beta - \beta n^-)/(\beta n' - \beta n^-)$, if $(\beta > \beta n^-)$ AND $(\beta \leq \beta n')$, $Wn(\alpha, \beta) = 0$, if $(\beta \leq \beta n^-)$.

6. A multislice CT apparatus comprising:
a detector including a plural number of detector elements arranged in an axial direction of the multislice CT apparatus;
a moving table on which an object to be examined is placed to be examined with a rotating X-ray source and at least ones of the plural number of detector elements, to acquire a plural number of spiral projection data;
a correction processing means for performing correction processes to the spiral projection data; and
an image reconstruction means for reconstructing a tomographic image from corrected spiral projection data;
wherein the correction processing means: has a weighting coefficient table storing a plural number of predetermined different multislice spiral weighting coefficients corresponding to predetermined ones of spiral pitch of a table moving amount at rotation against a row interval of the detector, and selects one of the plural number of predetermined different multislice spiral weighting coefficients in accordance with a predetermined spiral pitch at measurement for applying weighting to the spiral projection data of each row; has a means for generating spiral projection data for a virtual detector element in a different position from an actual detector element, and for applying a multislice spiral weighting to the spiral projection data for the virtual detector element; and, combines the spiral projection data after applying weighting application to each detector element or virtual detector element row.

7. A multislice CT apparatus as claimed in claim 6, wherein if a row number of actual detector elements in the detector is N and a spiral pitch is P, where P>N, then a number or rows used for each pitch increment including all actual detector elements and virtual detector elements is equal to P.

8. A multi-slice CT apparatus as claimed in claim 6 or claim 7, wherein when the virtual detector element is located between two actual detector elements, a weighting coefficient corresponding to the spiral projection data of the virtual detector element is determined from weighting coefficients of the two actual detector elements and applied to the two actual detector elements.

9. A multi-slice CT apparatus as claimed in claim 6 or claim 4, wherein when the virtual detector element is located outside an axial direction measuring region of the detector, and complementary data is used as projection data of the virtual detector element, a weighting coefficient corresponding to the complementary data is determined from weighting coefficients of neighboring actual detector elements, and applied to the neighboring actual detector elements.

10. A multislice X-ray CT apparatus as claimed in claim 6, in which the correction processing means comprises a plurality of weighting processing means for performing weighting processing for differing rows in parallel, with each weighting processing means including a weight coefficient memory to store a multislice spiral weighting coefficient selected from the weighting coefficient table, for a subject row to be processed.

11. A multislice X-ray CT apparatus as claimed in claim 6, in which the correction processing means generates the predetermined different multislice spiral weighting coefficients of the weighting coefficient table for each row by:
calculating a reference angle βs corresponding to a slice position for image reconstruction;
calculating a reference angle βn at each row;
calculating an upper limit βn⁺ and a lower limit βn⁻ based on a preset value M;
selecting a parameter G for controlling a weighting width, and calculating a range of weighting; and
applying at least one predetermined function to determine weighting Wn.

12. A multislice X-ray CT apparatus as claimed in claim 11, wherein at least one of:
the calculating of the reference angle βn at each row uses the equations:

$\beta 1 = \beta s + 1.5 \times \Delta \beta,$ $\beta 2 = \beta s + 0.5 \times \Delta \beta,$ $\beta 3 = \beta s - 0.5 \times \Delta \beta,$ $\beta 4 = \beta s - 1.5 \times \Delta \beta;$ the calculating of the an upper limit βn⁺ and the lower limit βn⁻ uses the equations:

$\beta n^+ = \beta n + \Delta \beta,$ $\beta n^- = \beta n - \Delta \beta;$ the calculating of the range of weighting uses the equations:

$\beta n' = \beta n + M\alpha,$ $\beta^+ = \beta n' + G \cdot \Delta \beta + M\alpha,$ $\beta^- = \beta n' - G \cdot \Delta \beta + M\alpha;$ the applying of the at least one predetermined function to determine the weighting Wn uses the equations:

$Wn(\alpha,\beta)=0$, if $(\beta \geq \beta n^+)$, $Wn(\alpha,\beta)=(\beta n^+ - \beta)/(\beta n^+ - \beta n')$, if $(\beta < \beta n^+)$ AND $(\beta > \beta n')$, $Wn(\alpha,\beta)=(\beta - \beta n^-)/(\beta n' - \beta n^-)$, if $(\beta > \beta n^-)$ AND $(\beta \leq \beta n')$, $Wn(\alpha,\beta)=0$, if $(\beta \leq \beta n^-)$.

13. A multislice CT apparatus comprising:
a detector including a plural number of detector elements arranged in an axial direction of the multislice CT apparatus;
a moving table on which an object to be examined is placed to be examined with a rotating X-ray source and at least ones of the plural number of detector elements, to acquire a plural number of spiral projection data;
a correction processor to perform correction processes to the spiral projection data; and
an image reconstructor to reconstruct a tomographic image from corrected spiral projection data;
wherein the correction processor has a weighting coefficient table storing a plural number of predetermined different multislice spiral weighting coefficients corresponding to predetermined ones of spiral pitch of a table moving amount at rotation against a row interval of the detector, and is arranged to select one of the plural number of predetermined different multislice spiral weighting coefficients in accordance with a predetermined spiral pitch at measurement to apply weighting to the spiral projection data of each row, and is arranged to combine the spiral projection data after applying weighting application to each detector element row.

14. A multislice X-ray CT apparatus as claimed in claim 13, in which the correction processor changes a weighting region of spiral projection data in accordance with the predetermined spiral pitch at measurement.

15. A multislice X-ray CT apparatus as claimed in claim 13, in which the correction processor comprises a plurality of weighting processors to perform weighting processing for differing rows in parallel, with each weighting processor including a weight coefficient memory to store a multislice spiral weighting coefficient selected from the weighting coefficient table, for a subject row to be processed.

16. A multislice X-ray CT apparatus as claimed in claim 13, in which the correction processing means generates the predetermined different multislice spiral weighting coefficients of the weighting coefficient table for each row by:
calculating a reference angle βs corresponding to a slice position for image reconstruction;
calculating a reference angle βn at each row;
calculating an upper limit $\beta n^+$ and a lower limit $\beta n^-$ based on a preset value M;
selecting a parameter G for controlling a weighting width, and calculating a range of weighting; and
applying at least one predetermined function to determine weighting Wn.

17. A multislice X-ray CT apparatus as claimed in claim 16, wherein at least one of:
the calculating of the reference angle βn at each row uses the equations:

$\beta 1 = \beta s + 1.5 \times \Delta \beta$, $\beta 2 = \beta s + 0.5 \times \Delta \beta$, $\beta 3 = \beta s - 0.5 \times \Delta \beta$, $\beta 4 = \beta s - 1.5 \times \Delta \beta$;

the calculating of the an upper limit $\beta n^+$ and the lower limit $\beta n^-$ uses the equations:

$\beta n^+ = \beta n + \Delta \beta$, $\beta n^- = \beta n - \Delta \beta$;

the calculating of the range of weighting uses the equations:

$\beta n' = \beta n + M\alpha$, $\beta^+ = \beta n' + G \cdot \Delta \beta + M\alpha$, $\beta^- = \beta n' - G \cdot \Delta \beta + M\alpha$;

the applying of the at least one predetermined function to determine the weighting Wn uses the equations:

$Wn(\alpha,\beta)=0$, if $(\beta \geq \beta n^+)$, $Wn(\alpha,\beta)=(\beta n^+ - \beta)/(\beta n^+ - \beta n')$, if $(\beta < \beta n^+)$ AND $(\beta > \beta n')$, $Wn(\alpha,\beta)=(\beta - \beta n^-)/(\beta n' - \beta n^-)$, if $(\beta > \beta n^-)$ AND $(\beta \leq \beta n')$, $Wn(\alpha,\beta)=0$, if $(\beta \leq \beta n^-)$.

18. A multislice CT apparatus comprising:
a detector including a plural number of detector elements arranged in an axial direction of the multislice CT apparatus;
a moving table on which an object to be examined is placed to be examined with a rotating X-ray source and at least ones of the plural number of detector elements, to acquire a plural number of spiral projection data;
a correction processor to perform correction processes to the spiral projection data; and
an image reconstructor to reconstruct a tomographic image from corrected spiral projection data;
wherein the correction processor: has a weighting coefficient table storing a plural number of predetermined different multislice spiral weighting coefficients corresponding to predetermined ones of spiral pitch of a table moving amount at rotation against a row interval of the detector, and is arranged to select one of the plural number of predetermined different multislice spiral weighting coefficients in accordance with a predetermined spiral pitch at measurement for applying weighting to the spiral projection data of each row; has a virtual generator to generate spiral projection data for a virtual detector element in a different position from an actual detector element, and to apply a multislice spiral weighting to the spiral projection data for the virtual detector element; and, is arranged to combine the spiral projection data after applying weighting application to each detector element or virtual detector element row.

19. A multislice CT apparatus as claimed in claim 18, wherein if a row number of actual detector elements in the detector is N and a spiral pitch is P, where P>N, then a number of rows used for each pitch increment including all actual detector elements and virtual detector elements is equal to P.

20. A multi-slice CT apparatus as claimed in claim 18 or claim 14, wherein when the virtual detector element is located between two actual detector elements, a weighting coefficient corresponding to the spiral projection data of the virtual detector element is determined from weighting coefficients of the two actual detector elements, and applied to the two actual detector elements.

21. A multi-slice CT apparatus as claimed in claim 18 or claim 19, wherein when the virtual detector element is located outside an axial direction measuring region of the detector, and complementary data is used as projection data of the virtual detector element, a weighting coefficient corresponding to the complementary data is determined from weighting coefficients of neighboring actual detector elements, and applied to the neighboring actual detector elements.

22. A multislice X-ray CT apparatus as claimed in claim 18, in which the correction processor comprises a plurality of weighting processors to perform weighting processing for differing rows in parallel, with each weighting processor including a weight coefficient memory to store a multislice spiral weighting coefficient selected from the weighting coefficient table, for a subject row to be processed.

23. A multislice X-ray CT apparatus as claimed in claim 18, in which the correction processing means generates the predetermined different multislice spiral weighting coefficients of the weighting coefficient table for each row by:

calculating a reference angle $\beta s$ corresponding to a slice position for image reconstruction;

calculating a reference angle $\beta n$ at each row;

calculating an upper limit $\beta n^+$ and a lower limit $\beta n^-$ based on a preset value M;

selecting a parameter G for controlling a weighting width, and calculating a range of weighting; and applying at least one predetermined function to determine weighting Wn.

24. A multislice X-ray CT apparatus as claimed in claim 23, wherein at least one of:

the calculating of the reference angle $\beta n$ at each row uses the equations:

$$\beta 1 = \beta s + 1.5 \times \Delta\beta,$$

$$\beta 2 = \beta s + 0.5 \times \Delta\beta,$$

$$\beta 3 = \beta s - 0.5 \times \Delta\beta,$$

$$\beta 4 = \beta s - 1.5 \times \Delta\beta;$$

the calculating of the an upper limit $\beta n^+$ and the lower limit $\beta n^-$ uses the equations:

$$\beta n^+ = \beta n + \Delta\beta,$$

$$\beta n^- = \beta n - \Delta\beta;$$

the calculating of the range of weighting uses the equations:

$$\beta n' = \beta n + M\alpha,$$

$$\beta^+ = \beta n' + G \cdot \Delta\beta + M\alpha,$$

$$\beta^- = \beta n' - G \cdot \Delta\beta + M\alpha;$$

the applying of the at least one predetermined function to determine the weighting Wn uses the equations:

$$Wn(\alpha,\beta)=0, \text{ if } (\beta \geq \beta n^+),$$

$$Wn(\alpha,\beta)=(\beta n^+ - \beta)/(\beta n^+ - \beta n'), \text{ if } (\beta < \beta n^+) \text{ AND } (\beta > \beta n'),$$

$$Wn(\alpha,\beta)=(\beta - \beta n^-)/(\beta n' - \beta n^-), \text{ if } (\beta > \beta n^-) \text{ AND } (\beta \leq \beta n'),$$

$$Wn(\alpha,\beta)=0, \text{ if } (\beta \leq \beta n^-).$$

* * * * *